(12) United States Patent
Ferchmin et al.

(10) Patent No.: US 9,259,411 B2
(45) Date of Patent: Feb. 16, 2016

(54) NEURONAL CIRCUIT-DEPENDENT NEUROPROTECTION BY INTERACTION BETWEEN NICOTINIC RECEPTORS

(71) Applicants: Peter Andrew Ferchmin, San Juan, PR (US); Vesna Ana Eterovic De Ferchmin, San Juan, PR (US); Hector Manuel Maldonado, Cidra, PR (US); Khalid El Sayed, West Monroe, LA (US)

(72) Inventors: Peter Andrew Ferchmin, San Juan, PR (US); Vesna Ana Eterovic De Ferchmin, San Juan, PR (US); Hector Manuel Maldonado, Cidra, PR (US); Khalid El Sayed, West Monroe, LA (US)

( * ) Notice: Subject to any disclaimer, the term of this patent is extended or adjusted under 35 U.S.C. 154(b) by 0 days.

(21) Appl. No.: 14/630,381

(22) Filed: Feb. 24, 2015

(65) Prior Publication Data

US 2016/0008315 A1 Jan. 14, 2016

Related U.S. Application Data

(60) Division of application No. 13/673,479, filed on Nov. 9, 2012, now Pat. No. 9,000,030, which is a continuation of application No. 12/308,293, filed on Feb. 10, 2009, now abandoned.

(60) Provisional application No. 60/816,683, filed on Jun. 27, 2006.

(51) Int. Cl.
*A61K 31/336* (2006.01)

(52) U.S. Cl.
CPC .................................. *A61K 31/336* (2013.01)

(58) Field of Classification Search
CPC ..................................................... A61K 31/336
USPC ........................................................... 514/475
See application file for complete search history.

*Primary Examiner* — Jennifer M Kim
(74) *Attorney, Agent, or Firm* — Harbin & Hein PLLC

(57) ABSTRACT

A method of inhibiting excitotoxicity by indirectly activating α4β2 nicotinic acetylcholine receptors (nAChRs) which indirectly activate synaptic AMPA and NMDA receptors is disclosed. Inhibitors of α7 nAChRs, such as macrocyclic diterpenoids, more specifically cembranoids or methyllycaconitine (MLA), indirectly activate α4β2 nAChRs and can be used to treat neurodegenerative diseases, including, but not limited to, Alzheimer's Disease, Parkinson Disease, AIDS related dementia and the delayed effects of stroke. They can also be used to treat diseases associated with neuronal impairment, including, but not limited to glaucoma caused by optical nerve damage, delayed effects of epilepsy; and multiple sclerosis.

5 Claims, 19 Drawing Sheets

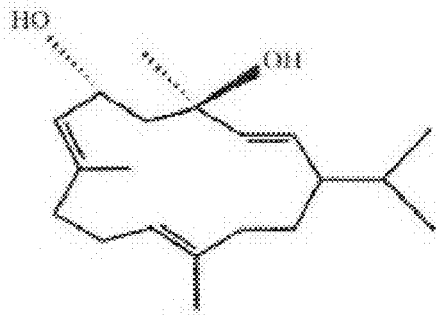
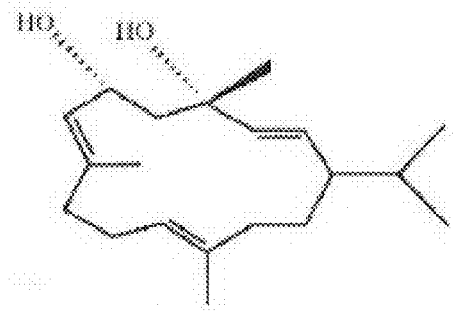
FIG. 1A  FIG. 1B
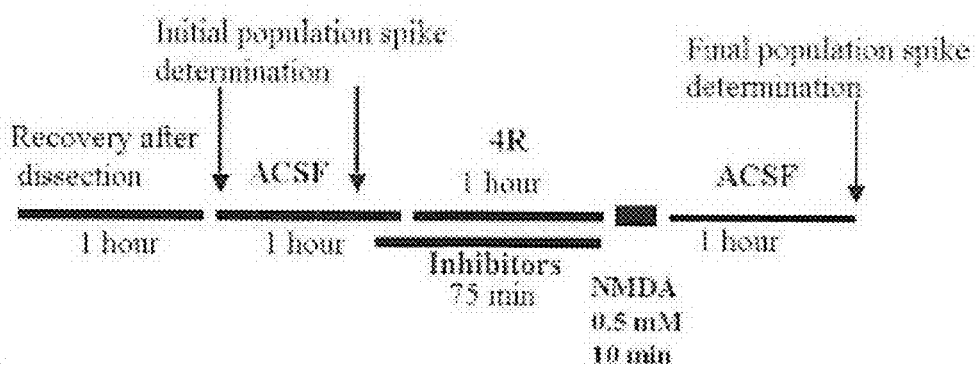
FIG. 2

NEURONAL CIRCUIT-DEPENDENT NEUROPROTECTION BY INTERACTION BETWEEN NICOTINIC RECEPTORS

RELATED APPLICATION

This invention is a divisional of U.S. application Ser. No. 13/673,479 filed Nov. 9, 2012 U.S. Pat. No. 9,000,030, which is a continuation of U.S. application Ser. No. 12/308,293 filed Feb. 10, 2009 (now abandoned) (published as US 2009/0291976 on Nov. 26, 2009), which claims the benefit of U.S. Provisional Application No. 60/816,683 filed Jun. 27, 2006. The entire teachings of the above applications are incorporated herein by reference.

GOVERNMENT SUPPORT

The invention was supported in part by grants from the following NIH Institutes: (a) NINDS and NCRR (SNRP Specialized Neuroscience Research Program, grant NS39408), (b) NIGMS (MBRS Minority Biomedical Research Support Program, grant S06GM50695), (c) NCRR (RCMI Research Centers in Minority Institutions, grant G-12RR03035.) The Government has certain rights in the invention.

BACKGROUND OF THE INVENTION

Neurodegenerative diseases, including Alzheimer's disease, Parkinson disease, AIDS-related dementia and the delayed effects of stroke, share one important element: neuronal death (death of nervous system cells) by a common mechanism called excitotoxicity.

Excitotoxicity results from excessive stimulation of glutamate receptors, particularly a subtype of glutamate receptors which specifically responds to the synthetic compound N-methyl-D-aspartate (NMDA). The NMDA receptor is a protein embedded in the cell membrane and containing in its structure a channel for positive ions. When the receptor is activated by glutamate, a channel opens and allows calcium ions ($Ca^{2+}$) to enter the cell. Excessive activation of this receptor allows too much $Ca^{2+}$ to enter the cell and this excess of $Ca^{2+}$ leads to cell death. Most of the ensuing neuronal death is a particular kind of cell death called apoptosis. Apoptosis results from the activation by $Ca^{2+}$ of built-in physiological mechanisms called the pro-apoptotic cell signaling pathways. Neuronal death results in impaired nervous system function such as impaired memory (Alzheimer's disease) and impaired coordination of movements (Parkinson disease).

Recent studies involving neuroprotection from excitotoxicity have suggested that activation of $\alpha 7$ nicotinic acetylcholine receptors (nAChR) mediates neuroprotection. For example, it has been reported that activation of $\alpha 7$ nAChRs on GABAergic interneurons evokes both dendritic and somatic inhibition of hippocampal neurons (Buhler A V and Dunwiddie T V Neurosci: 106:55-67 (2001). The fact that inhibition of $\alpha 7$ receptors decrease GABA input to cholinergic neurons (Giorgetti et al., Eur J Neurosci 12(6):1941-8 (2000); Materi, L. M., and Semba K., Eur J Neurosci 14:38-46 (2001)) support this idea.

Based on these facts, various pharmaceutical companies have attempted to develop drugs that ameliorate the effects of excitotoxicity using direct inhibitors of the NMDA receptor.

One NMDA receptor antagonist, the drug memantine, described in (Aracava, Y., et al., J Pharm Exp Ther 312:1195-1205 (2005)), has been approved for treatment of Alzheimer's disease. One recent study, however, has suggested that memantine may not be effective at treating Alzheimer's disease, especially during the early states of the disease, because memantine is a more potent inhibitor of al nAChRs than NMDA receptors. (Aracava, Y., et al., J Pharm Exp Ther 312:1195-1205 (2005)). The authors of this study reasoned that because $\alpha 7$ nAChRs agonists protect neurons against NMDA-induced excitotoxicity, use of an $\alpha 7$ antagonist may be counterproductive in treating Alzheimer's Disease. As highlighted by Aracava et al., there is confusion in the art regarding the mechanisms important for neuroprotection.

SUMMARY OF THE INVENTION

The present invention is based on Applicants' studies demonstrating that there are two different nicotinic pathways of neuroprotection and that under one of the two pathways, inhibition of $\alpha 7$ nAChRs is neuroprotective. The current invention also relates to a method of inhibiting excitotoxicity wherein $\alpha 4 \beta 2$ nicotinic acetylcholine receptors (nAChRs) are indirectly activated by an inhibitor of $\alpha 7$ nAChRs, such as macrocyclic diterpenoids, exemplified in this application by tobacco cembranoids. All macrocyclic diterpenoids share a basic structural similarity that likely translates into similar biological functions. Thus, it is reasonable to believe that as a class of compounds sharing structural similarities, macrocyclic diterpenoids, share some biological activities, specifically inhibition of $\alpha 7$ nAChRs. Although the application may specifically refer to cembranoids, it is understood that the term encompasses class of compounds known as macrocyclic diterpenoids, the basic structure of which is exemplified in FIGS. 13A-13C.

Nicotine has been reported to be neuroprotective in experimental and epidemiological studies. In addition to nicotine, tobacco and cigarette smoke contain macrocyclic diterpenoids, more specifically, cembranoids, which are antagonists of neuronal nicotinic receptors (nAChR). Exposure of hippocampal slices to N-methyl-D-aspartate (NMDA) decreases the population spikes (PS). This parameter has been used as a measure of excitotoxicity. Surprisingly, both nicotine and tobacco cembranoids protected against NMDA and this neuroprotection was not blocked by methyllycaconitine (MLA), an antagonist of $\alpha 7$ nAChR. On the contrary, MLA had a neuroprotective effect of its own. The effect of the tobacco cembranoid (1S,2E,4R,6R,7E,11E)-cembra-2,7,11-triene-4,6-diol (4R) on the neuroprotection against NMDA was examined. Dihydro-Beta-erithroidine (DHβE), a selective antagonist of $\alpha 4 \beta 2$ nAChR, inhibited the neuroprotection by nicotine, 4R, and MLA, suggesting the involvement, of $\alpha 4 \beta 2$ nAChRs in the neuroprotection. The cell-signaling pathways underlying the neuroprotection by 4R and by nicotine are different. The activity of phosphatidylinositol-3 kinase (PI3K) was required in both cases; however, 4R required the activity of L-type calcium channels and CAM kinase, whereas nicotine required the extracellular signal regulated kinase-1,2 (ERK) and protein kinase C(PKC). In addition, 4R did not enhance total phospho-ERK-1/2 but increased the amount of total Akt/PKB phosphorylated on the activation site and of glycogen synthase kinase 3-beta phosphorylated on the inhibitory site. Total levels of phosphoenzymes are presented instead of the ratio of phospho-over total enzyme because in preliminary experiments total ERK-1/2 levels were slightly increased by 4R. These findings demonstrate that there are two different nicotinic neuroprotective mechanisms mediated by direct or indirect activation $\alpha 4 \beta 2$ nicotinic receptors.

A described herein, it has been demonstrated that both the direct and indirect $\alpha 4 \beta 2$ dependent neuroprotective mechanisms require activation of the AMPA/kainate type glutamate receptor (hereinafter AMPA receptor). However, the two different α4β2 dependent neuroprotective mechanisms are differentiated not only via direct versus indirect activation of the α4β2 nicotinic receptors, but also with respect to the dependence on the NMDA subtype of glutamatergic receptor (hereinafter "NMDA receptor" or "NMDA-R"). The neuroprotection initiated by α7 inhibitors is annulled by competitive inhibitors of the NMDA receptors while the neuroprotection by nicotine does not depend on the activity of NMDA receptors. This novel mechanism whereby α7 inhibitors neuroprotect indirectly through a synaptic circuit involving α4β2 receptors thereby activating two glutamate receptors, wherein one of the receptors is a subsynaptic NMDA receptor and the other is a subsynaptic AMPA receptor, leading to neuroprotection, is described herein. Activation of the glutamate receptors NMDA and AMPA can be substantially simultaneous activation. However, these two receptors are often co-localized at the same synapse and the activation of AMPA receptor facilitates the synaptic activation of the NMDA receptor by removing its inhibition by $MG^{2+}$. Therefore, if the two receptors are co-localized, the activation can be sequential with AMPA receptor activation prior to NMDA receptor activation. As used herein, when the phrase e.g., "activation of at least one AMPA receptor and at least one NMDA receptor" is described, both activation scenarios are encompassed.

In particular, macrocyclic; diterpenoids activate at least one AMPA receptor and at least one NMDA receptor by a mechanism that comprises the steps of inhibiting at least one α7 neuronal nicotinic acetylcholine receptor, activating at least one α4β2 neuronal nicotinic acetylcholine receptor, and activating at least one AMPA receptor and at least one NMDA receptor, wherein activation of the receptors is concomitant.

Thus, while not wishing to be bound by theory, the mechanism can be described as inhibiting at least one al neuronal nicotinic acetylcholine receptor which in turn decreases the release of GABA from interneurons. This decrease in GABA release increases acetylcholine release which, in turn, activates at least one α4β2 neuronal nicotinic acetylcholine receptor. Activation of at least one α4β2 neuronal nicotinic acetylcholine receptor increases glutamate release which activates at least one AMPA receptor and at least one NMDA receptor. The activation of the at least one AMPA receptor and at least one NMDA receptor triggers an antiapoptotic cell-signaling pathway, thus activating Akt/PKB by phosphorylation, which, in turn, inactivates glycogen synthase kinase 3 (GSK-3) by phosphorylation, resulting in the inhibition of neuronal apoptosis leading to neuroprotection.

Thus, based on these studies, Applicants, in one embodiment of the present invention, have elucidated novel methods of inhibiting apoptosis in a neuron for example in vivo or ex vivo, as in its native environment, e.g., in contact with other cells, by contacting the neuron with at least one macrocyclic diterpenoid, or a biologically active fragment, analog, or derivative thereof, wherein the macrocyclic diterpenoid activates at least one α4β2 neuronal nicotinic acetylcholine receptor (nAChr) which indirectly activates at least one AMPA receptor and at least one NMDA receptor.

In another embodiment, Applicants have elucidated novel methods of treating or preventing neuronal damage in a subject by administering at least one macrocyclic diterpenoid, or a biologically active fragment, analog, or derivative thereof.

In yet another embodiment, Applicants describe a novel method of inhibiting excitotoxicity in a mammal by activating at least one α4β2 nAChR which indirectly activates at least one AMPA receptor and at least one NMDA receptor by administering to the mammal at least one macrocyclic diterpenoid, or a biologically active fragment, analog, or derivative thereof.

BRIEF DESCRIPTION OF THE DRAWINGS

FIGS. 1A and 1B. Structures of two tobacco cembranoids: 4R (FIG. 1A) (1S,2E,4R,6R,7E,11E)-cembra-2,7,11-triene-4,6-diol and 4S (FIG. 1B) (1S,2E,4S,6R,7E,11E)-cembra-2,7,11-triene-4,6-diol are depicted.

FIG. 3A-1 is a graph showing that NMDA receptor-mediated population spikes (PSs) are not affected by 2 µM 4R. Hippocampal slices were supervised with 50 µM DNQX in ACSF to pharmacologically isolate the NMDA receptor-mediated PSs from the component mediated by the AMPA/kainate receptors. Field potentials were recorded in s. pyramidale of area CA1 after electric stimulation of incoming afferents in s. radiatum. Recordings of field potentials before (Trace A), during (Trace B), and after (Trace C) 2 µM 4R application are respectively shown in FIG. 3A-2. Each recording is an average of the last five recordings of each condition. APV (50 µM) was applied to show the dependence of the PS on the NMDA receptor (Trace D) (FIG. 3A-2). The calibration bar is 2 mV by 4 msec. The plot of the time course of the individual PSs is shown in E. Stimulus artifacts were removed.

FIG. 3B-1 is a graph showing that the initial slopes of the population EPSPs mediated by NMDA receptors are not inhibited by 2 and 20 µM 4R. Pharmacologically isolated NMDA receptor-mediated population excitatory postsynaptic potentials (EPSPs) were recorded in the presence of 50 µM DNQX from s. radiatum after stimulation of incoming fibers. The waveforms shown are the average of the last five recordings of each treatment. FIG. 3B-2 respectively shows Trace A: Before application of 4R; Trace B: In the presence of 2 µM 4R; Trace C: In the presence 20 µM 4; and Trace D: Effect of inhibition of the NMDA receptor by 50 µM APV. The calibration bars are 0.5 mV.times.5 msec. The time course of the initial slope of the population EPSPs is shown in E. Some rundown of the slice was observed as well as a complete block by APV.

FIG. 3C-1 is a graph showing the effect of 4R applied before NMDA on PS recovery. PSs in normal ACSF, without inhibitors of glutamate receptors, were recorded from CA1. FIG. 3C-2 respective shows Trace A: Average of 30 recordings in ACSF; Trace B: Average of 60 recordings in the presence of 2 µM 4R; Trace C: Block of response after 0.5 mM NMDA application is shown as the average of the recordings beginning when NMDA completely blocked the responses and before the onset of recovery; and Trace D: Recovery of the response after NMDA washout. The calibration bars are 5 mV×2 msec. E: Plot of the time course of the area of the PSs in the conditions indicated.

Figure 5:
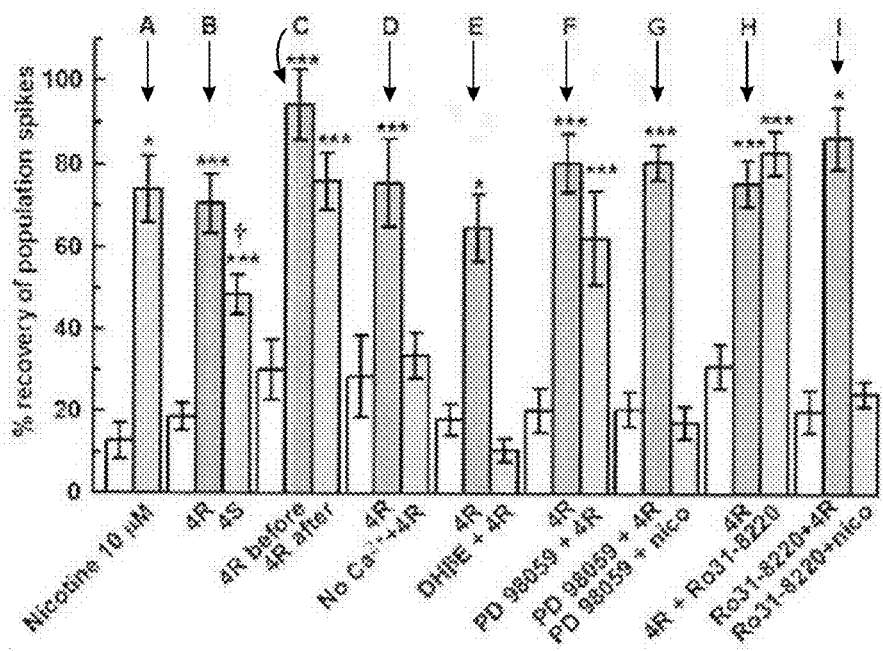
FIG. 5. Bar graphs (A)-(I) of FIG. 5 depict neuroprotection against NMDA toxicity by tobacco cembranoids. The white bars represent the percent recovery of PSs 1-2 hr after perfusing with 0.5 mM NMDA. This condition, referred to as NMDA control, shows the effect of NMDA toxicity in unprotected slices. The gray bars represent the recovery after additional treatments.

Bar Graph (A) of FIG. 5: The effect of NMDA and the neuroprotection provided by preincubation with nicotine is shown.

Bar Graph (B) of FIG. 5: 20 μM 4R or 4S were applied for 1 hr before application of 0.5 mM NMDA. Both cembranoids significantly, protected the recovery of PSs against NMDA (***P<0.001; n=35 per group). Slices treated with 4R recovered 71% of the original PS and those treated with 4S, 49%; the difference between both isomers was significant (†P<0.005).

Bar Graph (C) of FIG. 5: The neuroprotective effect of 2 μM 4R was significant when applied for 1 hr either before or after the standard NMDA treatment (***P<0.001; n=21 in all groups).

Bar Graph (D) of FIG. 5: Ca$^{2+}$ in the ACSF was required during the preincubation with 2 μM 4R to mediate neuroprotection. 4R was applied during 1 hr in the absence of Ca$^{2+}$. After 4R application, normal Ca$^{2+}$-ACSF was reapplied until PSs reappeared and reached the initial size, and 0.5 mM NMDA was applied for 10 min. The total incubation time before and after NMDA was the same for the three conditions. The recovery of PSs in NMDA controls and in slices preincubated with 4R in the absence of external Ca.sup.2+ before NMDA were not different from each other, but significantly different from slices preincubated with 2 μM 4R in the presence of 2 mM Ca$^{2+}$ before NMDA (***P<0.002; n=14 slices per group).

Bar Graph (E) of FIG. 5: The neuroprotection by 2 μM 4R NMDA was inhibited by 1 μM DHβE (*P<0.05; n=21 slices per group). DHβE was perfused alone for 15 min followed by 1 hr perfusion together with 2 μM 4R.

Bar Graphs (F)-(I) of FIG. 5: The neuroprotection by 4R and nicotine are differentially affected by inhibitors of MEK-1,2 and PKC.

Bar Graph (F) of FIG. 5: The MEK-1,2 inhibitor 50 μM PD98059 did not abolish the neuroprotection by incubation of slices with 2 μM 4R for 1 hr before NMDA. The slices treated with 4R alone or in the presence of 50 μM PD98059 did not show significant differences among themselves, but their recovery was significantly larger than that of the NMDA controls (***P<0.002; n=21).

Bar Graph (G) of FIG. 5: PD98059 differentially affected neuroprotection by 2 μM 4R and 1 μM nicotine. Slices incubated with 4R in the presence PD98059 recovered significantly better (***P<0.001; n=21) but the slices treated with 1 μM and nicotine did not recover more than NMDA controls.

Bar Graph (H) of FIG. 5: 4R neuroprotection was not inhibited by 100 nM Ro-31-8220 (***p<0.001; n=21).

Bar Graph (I) of FIG. 5: Ro-31-8220 did not affect the neuroprotection by 2 μM 4R but annulled the neuroprotection by 1 μM nicotine. The recovery after preincubation with 2 μM 4R in the presence of 100 nM R0-31-8220 was significantly larger than that in slices treated with NMDA only (*P<0.05; n=21) but the recovery after preincubation with 1 μM nicotine in the presence of 100 nM R0-31-8220 was equal to recovery of NMDA controls.

Figure 6:
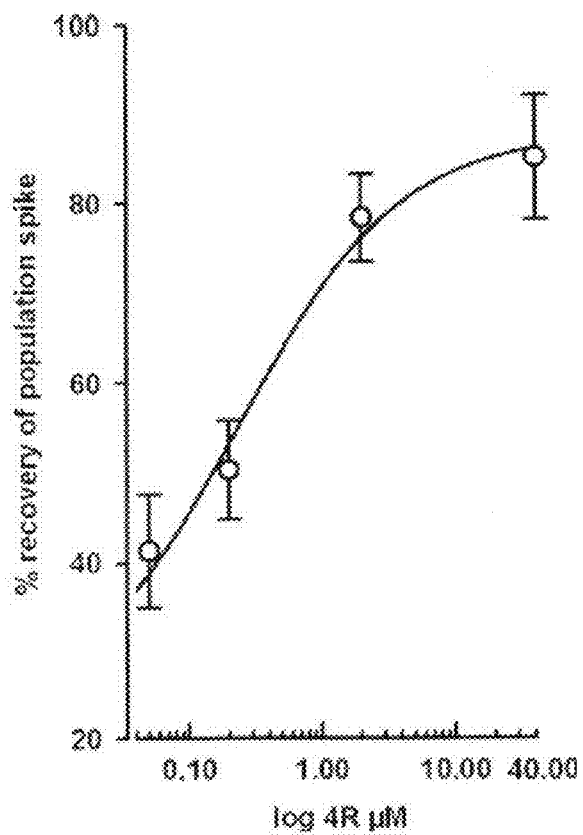

FIG. 6 is a graph showing the effect of 1 hr pretreatment with 0.05, 0.2, 2, or 40 μM 4R before 0.5 mM NMDA application on the recovery of the population spikes (PSs). The percent recovery of controls was 22.6.+−.3.5. Data were not normally distributed; therefore, the Kruskal-Wallis one way analysis of variance on ranks followed by Dunn's test was used and the significance level was set to P<0.05. Only the 0.05 μM 4R group was not significantly different from NMDA controls. The 40 μM group was significantly different from 0.05 and 0.2 μM 4R. The number of slices per experimental group was 70 for slices treated with NMDA alone and 35, 28, 49, and 21 for slices pretreated with ascending order of 4R concentration. The dose response was fitted to a Hill equation with four parameters $f(x)=y0+([a*x^b]/[c^b+x^b])$, where $y0=23.2.+−.4.5$ is the percent recovery in NMDA controls, $a=64.7.+−.7.9$ is the maximum recovery minus y0, $b=0.72.+−.0.2$ is the Hill coefficient, and $c=0.24.+−.0.12$ is the $EC_{50}$.

Figure 7:
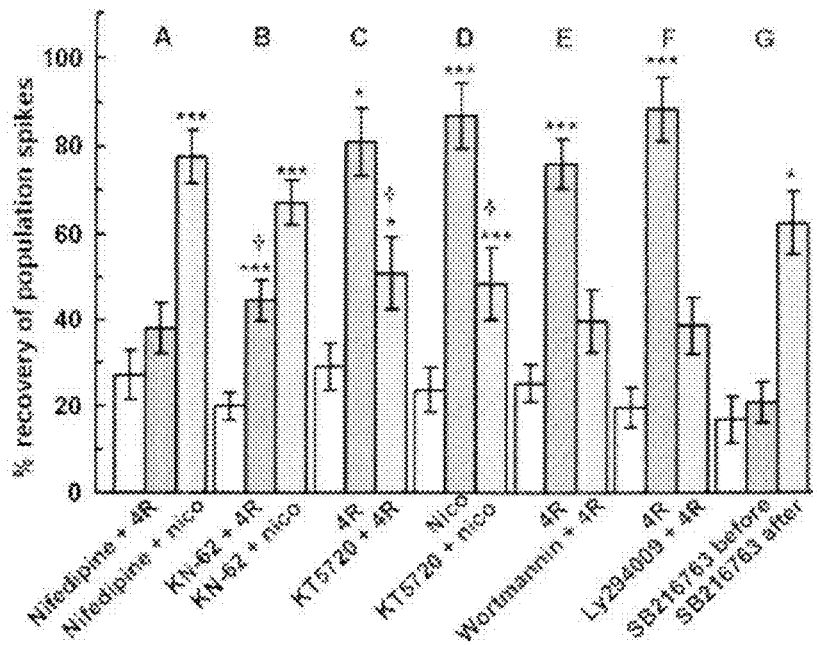

FIG. 7. Bar graphs (A)-(G) of FIG. 7 show that 4R neuroprotection depends on L-type Ca$^{2+}$ channels and partially on CaM kinase. The white bars without labels represent the percent recovery of population spikes (PSs) 1-2 hr after perfusing with 0.5 mM NMDA.

Bar graph (A) of FIG. 7: Nifedipine (10 μM) inhibited the neuroprotective effect of 4R but the neuroprotection by nicotine was not affected (***P<0.001; n=21 for all groups).

Bar graph (B) of FIG. 7: In the presence of 9 μM KN-62, a CaM kinase inhibitor, the recovery of PSs by 4R was significantly larger than that in NMDA controls (*P<0.001) although it was significantly lower than that of nicotine (†P<0.001). KN-62 did not prevent a significant neuroprotection by nicotine (*P<0.001; n=28 for all groups).

Bar graph (C) of FIG. 7: KT5720 (0.5 μM), a PKA inhibitor, partially but significantly decreased the neuroprotection by 2 μM 4R. Slices preincubated with 4R recovered significantly better (*P<0.05), than did NMDA controls and 4R plus KT5720 pretreated slices. The latter recovered significantly less than those pretreated with 4R only (†P<0.05).

Bar graph (D) of FIG. 7: A similar effect of KT5720 was observed for nicotine. The neuroprotective effect of 1 μM nicotine, with or without KT5720, was significant (***P<0.001) but KT5720 significantly decreased neuroprotection (†P<0.02). PI3K kinase inhibitors, 10 nM wortmannin and 10 μM LY294002, inhibited the neuroprotective effect of 2 μM 4R against NMDA.

Bar graph (E) of FIG. 7: 4R was significantly neuroprotective against NMDA (***P<0.001; n=21) and wortmannin inhibited the effect of 4R.

Bar graph (F) of FIG. 7: 4R mediated a significant neuroprotection (***P<0.001; n=20) and 4R plus Ly294002 treated slices showed a recovery that was not significantly different from NMDA controls.

Bar graph (G) of FIG. 7: 100 μM SB 216763, and inhibitor of the proapoptotic enzyme GSK3, was applied either 1 hr before or after application of 0.5 mM NMDA. SB 216763 was neuroprotective only when applied after NMDA (*P<0.05; n=21).

Figure 8:
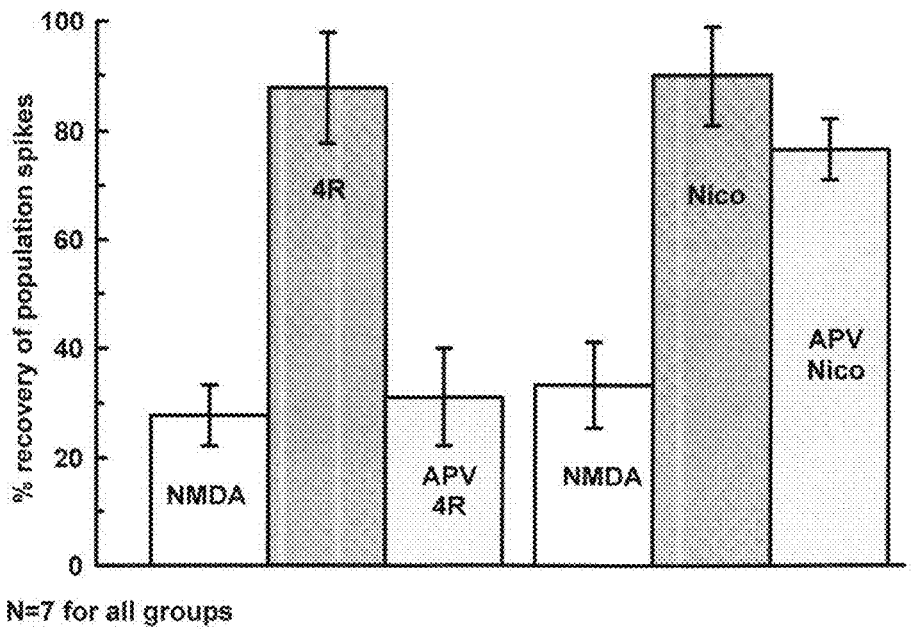

FIG. 8 represent the effect of 4:M (5-amino-1-phosphonovaleric acid) APV on the neuroprotection by either 2:M 4R or 1:M nicotine (Nico). The experimental design followed was as shown in FIG. 2. The white bars represent the recovery of function of slices treated only with NMDA. The dark gray bars show the recovery of slices exposed for 1 hour to 4R or Nico before the noxious exposure to NMDA. The lightly gray bars show the effect of 4R and nicotine when incubated in the presence of 0.4 μM APV. From this Fig it is concluded that APV robustly inhibits the effect of 4R but causes only a nonsignificant decrement of the nicotine mediated neuroprotection.

Figure 9:
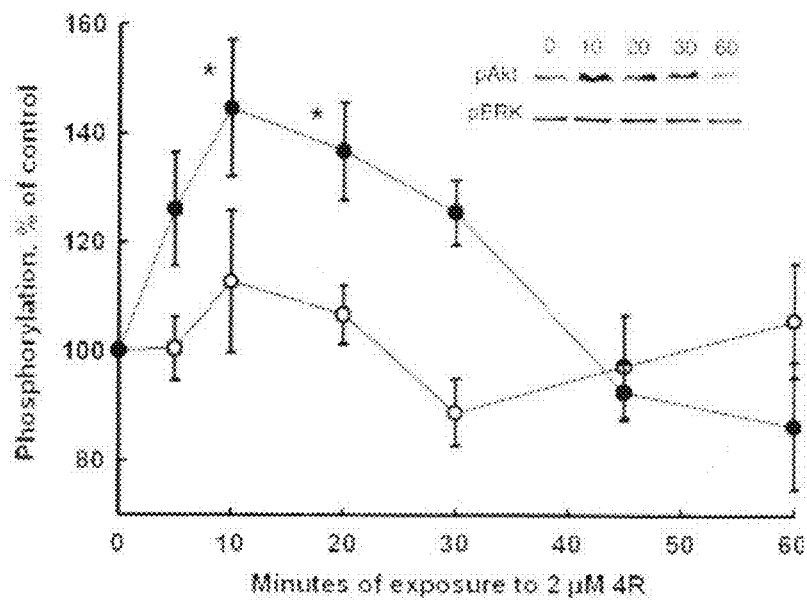

FIG. 9 is a graph showing the differential time course of ERK-1,2 and Akt phosphorylation in the presence of 2 μM 4R. The phosphorylation of Thr183 and Tyr185 of ERK (open circles) was not significantly affected by the presence of 4R; however, there was a significant increase over controls in the phosphorylation of Akt Ser473 (black circles) at 10 and 20 min (*P<0.05). The number of independent replications of phospho ERK-1,2 determinations in increasing order of incubation time from 5 to 60 min was 5, 7, 14, 8, 3, and 6 and for Akt 4, 6, 12, 6, 3, and 5. There was nonsignificant change with time in the phosphorylation of control slices kept in, ACSF. Insert at the top illustrates a typical Western blot result of an experiment from which the measurements represented in the graph were obtained. The numbers indicate minutes of exposure to 4R.

Figure 10:
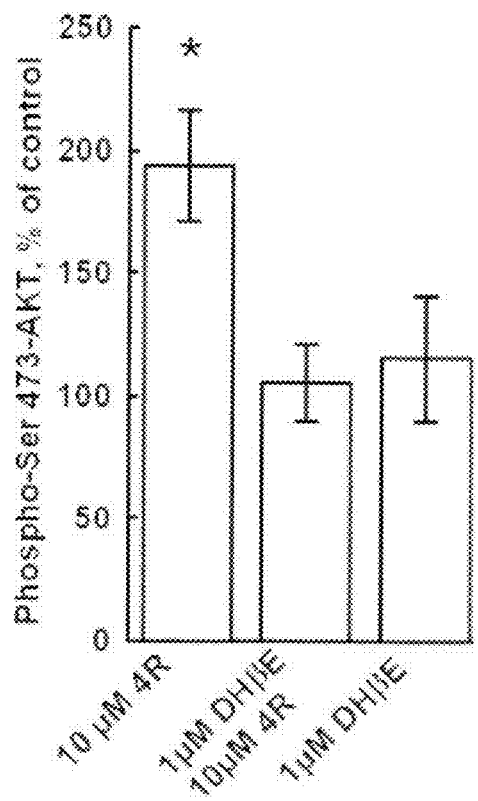

FIG. 10 is a bar graph showing that DHβE inhibits the phosphorylation of Ser473 of Akt mediated by 10 μM 4R. Slices were incubated for 20 min in ACSF either with 10 μM 4R, 10 μM 4R plus 1 μM DHβE, or 1 μM DHβE. Controls were incubated in normal ACSF. There were seven independent replications. The slices incubated with 10 μM 4R displayed significantly more Akt phosphorylation than did controls or those incubated in the presence of DHβE (*P<0.01).

Figure 11:
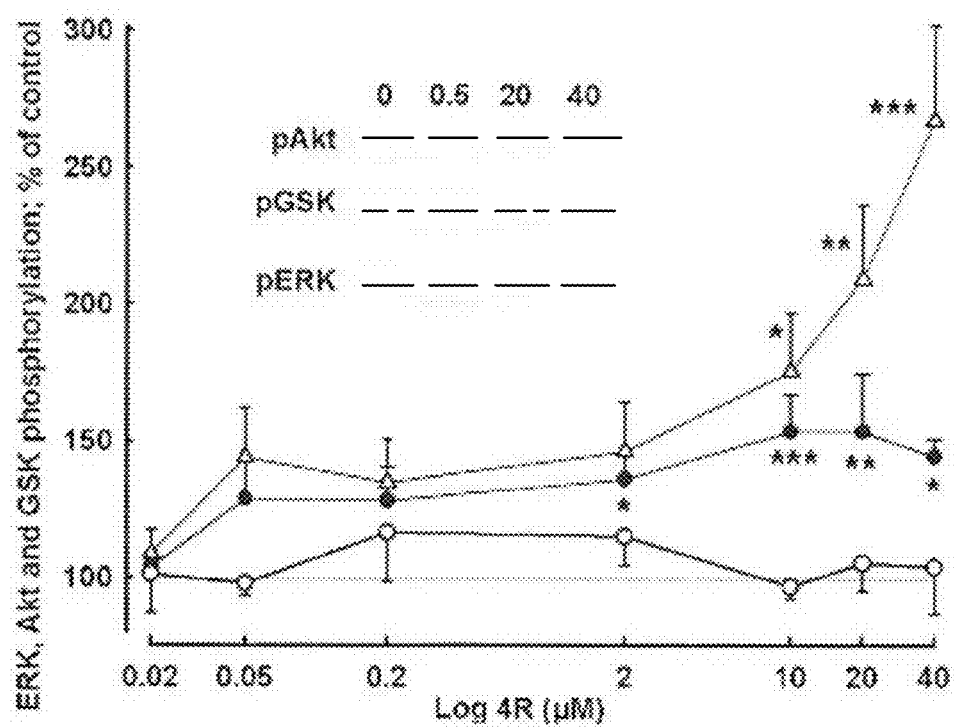

FIG. 11 is a graph showing the dose-response curve of the effect of 4R on activation by phosphorylation of Akt, GSK3, and ERK-1,2. Slices were exposed for 20 min to 4R at the concentrations indicated and phosphorylation of Akt Ser473 (dark circles), GSK3b Ser9 (triangles), and ERK-1,2 Thr183 and Tyr185 (open circles) were measured by Western blots. Insert at the top illustrates a typical Western blot result of an experiment from which the measurements represented in the graph were obtained. For simplicity, only control and three 4R concentrations are illustrated. A significant increase in activation of both Akt and GSK3 was observed when slices were exposed to 4R at concentrations higher than 2 or 10 μM, respectively. 4R failed to activate ERK at all concentrations tested. Each measurement represents the average of 3-13 independent determinations and statistical significance are as indicated (*P<0.05; P<0.01; *P<0.001).

Figure 12:
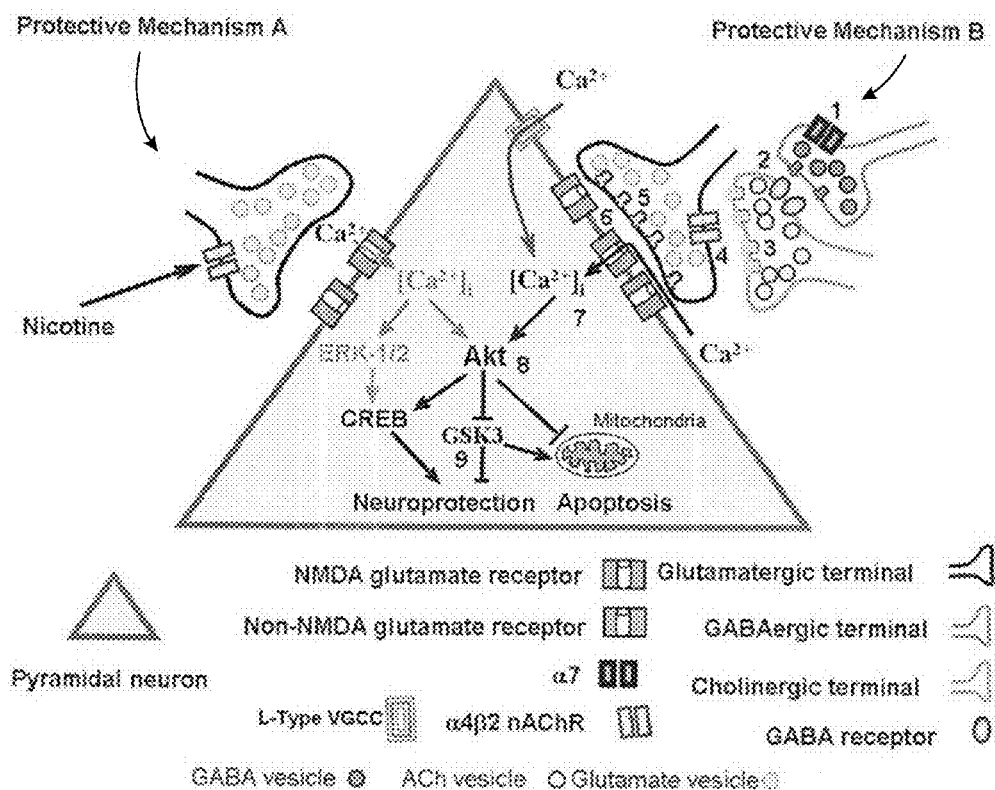

FIG. 12 is a diagram of a model of two neuroprotective mechanisms (A and B) mediated by α4β2 nicotinic receptors. Mechanism A: Nicotine activates the α4β2 nicotinic receptors located on the presynapses of glutamatergic neurons, thus increasing glutamate release and consequently increasing the activation of the postsynaptic glutamate receptors of the non-NMDA type; $Ca^{2+}$ entry through these receptors activates the cell-signaling pathway A. Mechanism B: 4R (or MLA, or memantine) inhibits the α7 receptor on GABAergic terminals [1], thus decreasing the release of GABA from interneurons [2]. The decreased GABAergic inhibition on cholinergic terminals increases acetylcholine release [3] and increases synaptic stimulation of a subsynaptic pool of α4β2 receptors [4], which increases the release of glutamate [5], which activates NMDA and AMPA receptors [6] located on pyramidal (principal) neurons. The consequent local depolarization activates voltage-gated calcium channels (VGCC). $Ca^{2+}$ entering through VGCC and through glutamate receptors [7] triggers cell-signaling pathway. Akt is activated by $Ca^{2+}$[8] and Akt activates CREB, inhibits the proapoptotic GSK-3, and inhibits mitochondria dependent apoptosis.

Figure 13A:
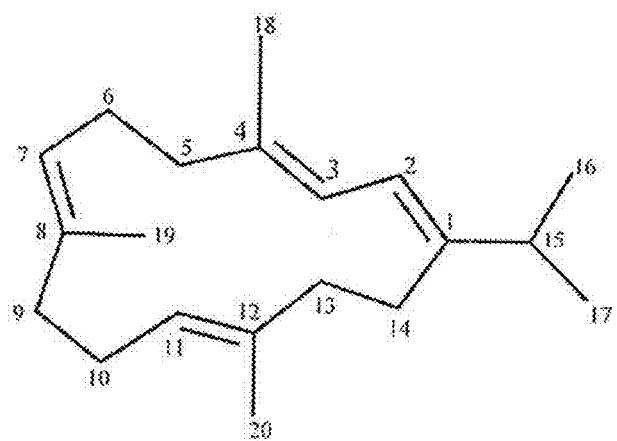
Figure 13B:
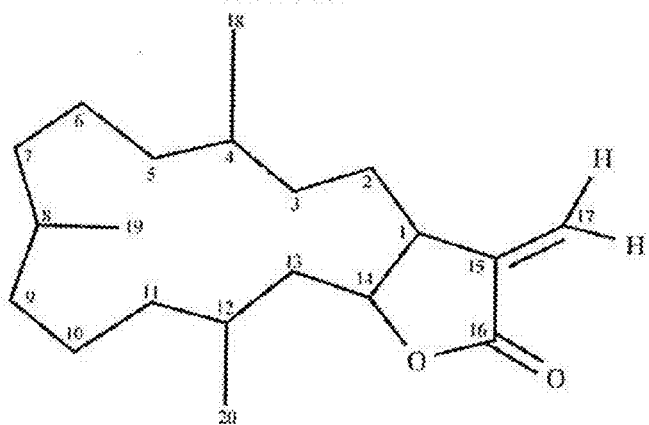
Figure 13C:
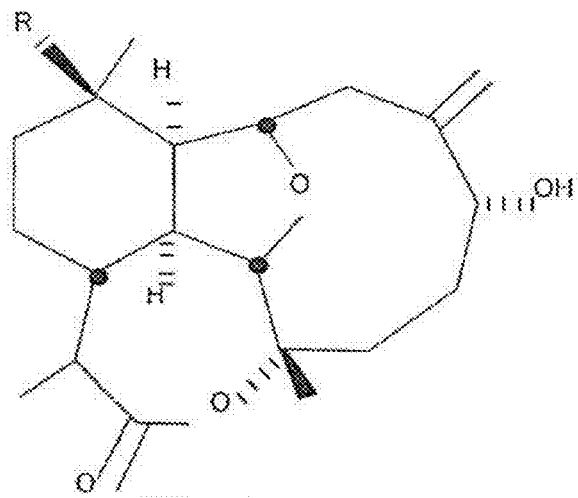

FIGS. 13A-13C. These figures are diagrams of examples of general macrocyclic diterpenoid structures.

Figure 14:
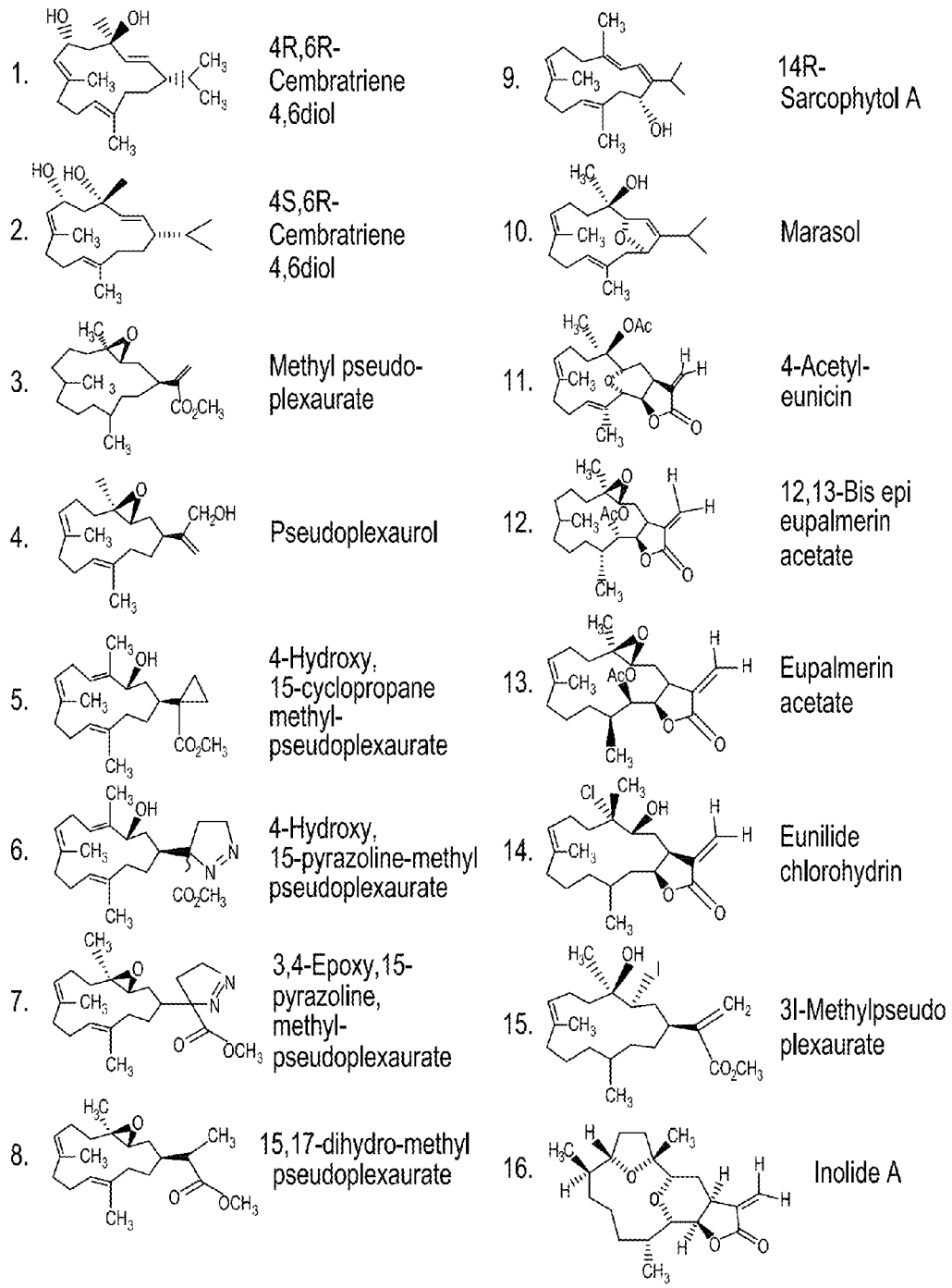
Figure 14:
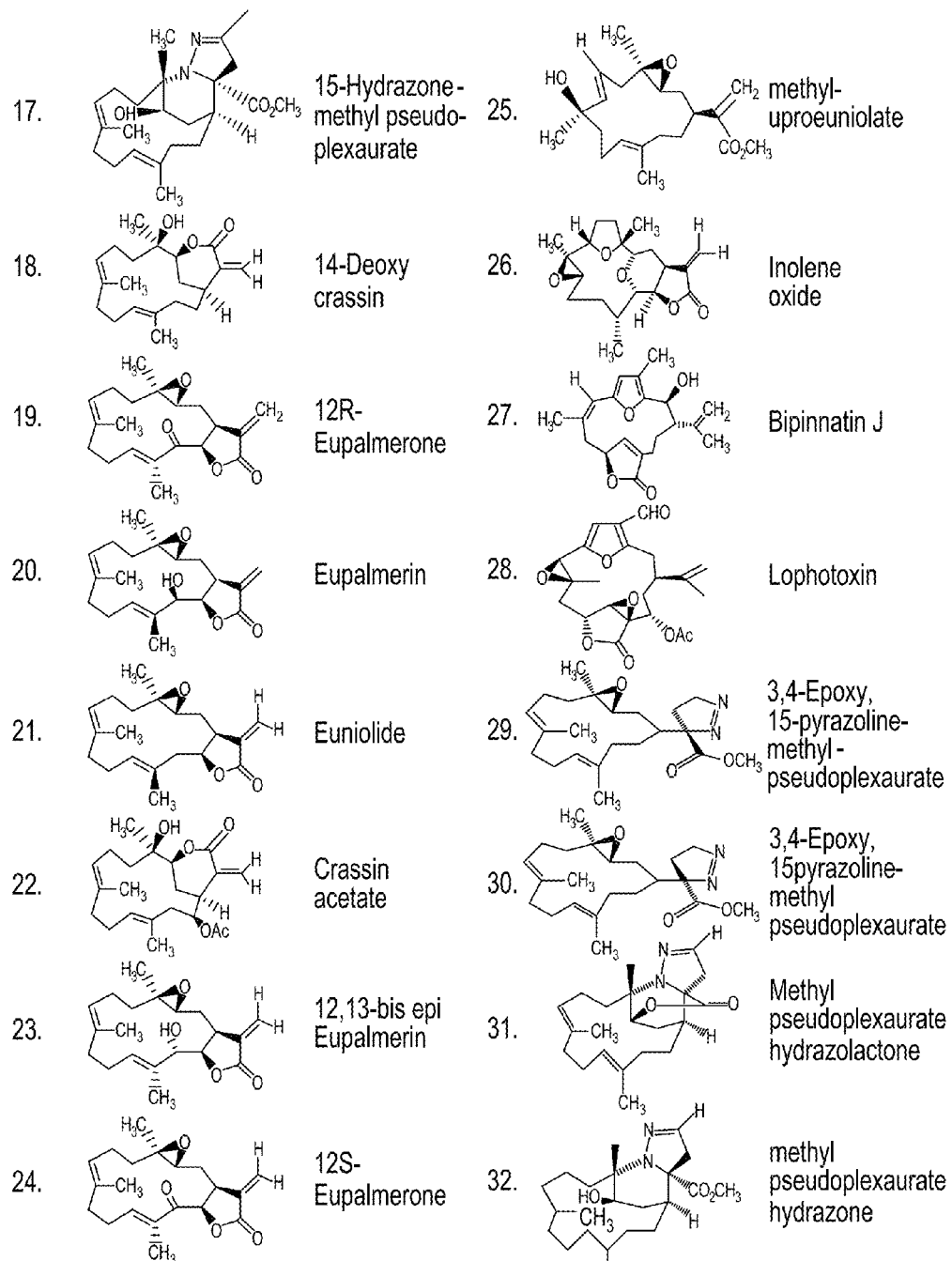
Figure 14:
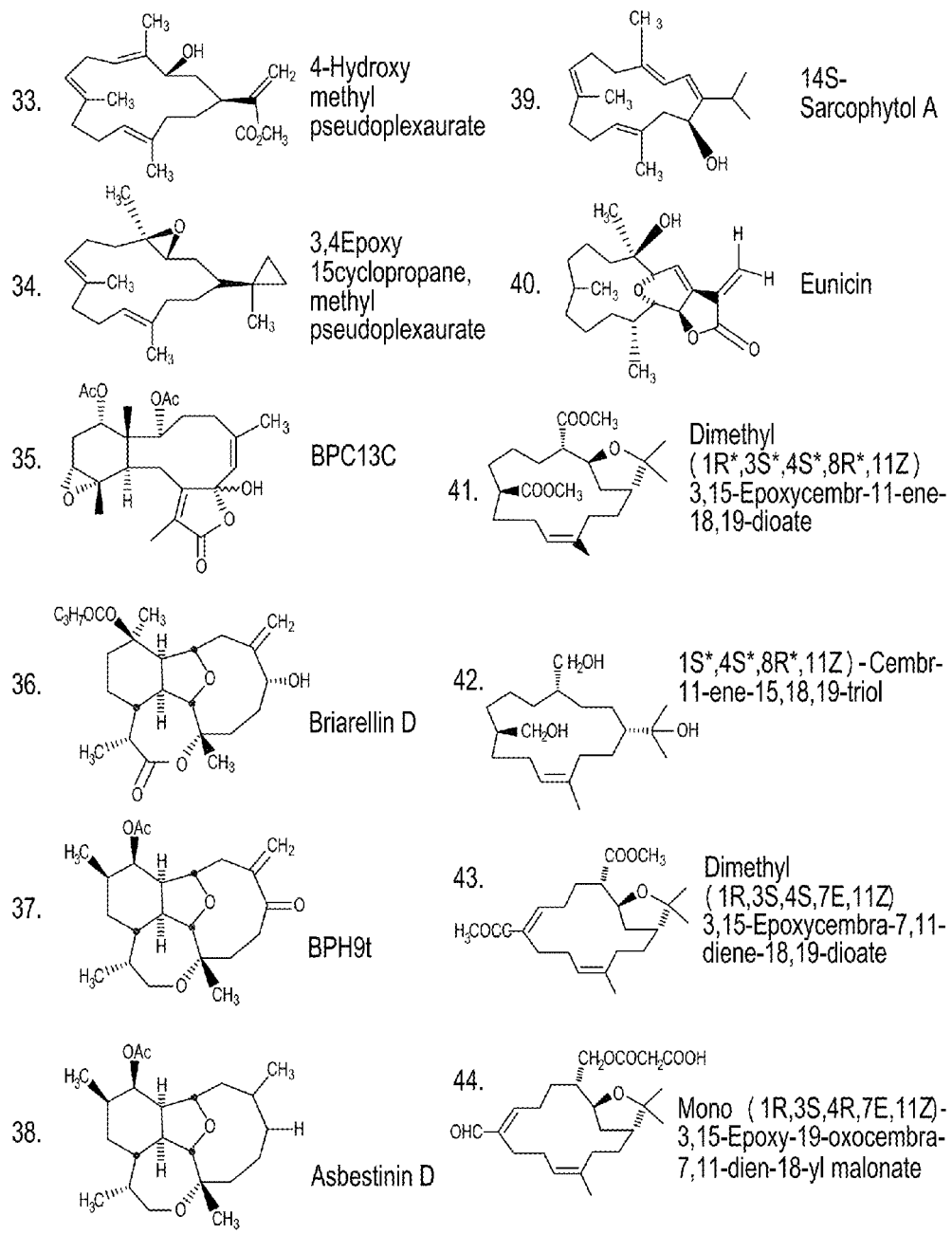
Figure 14:
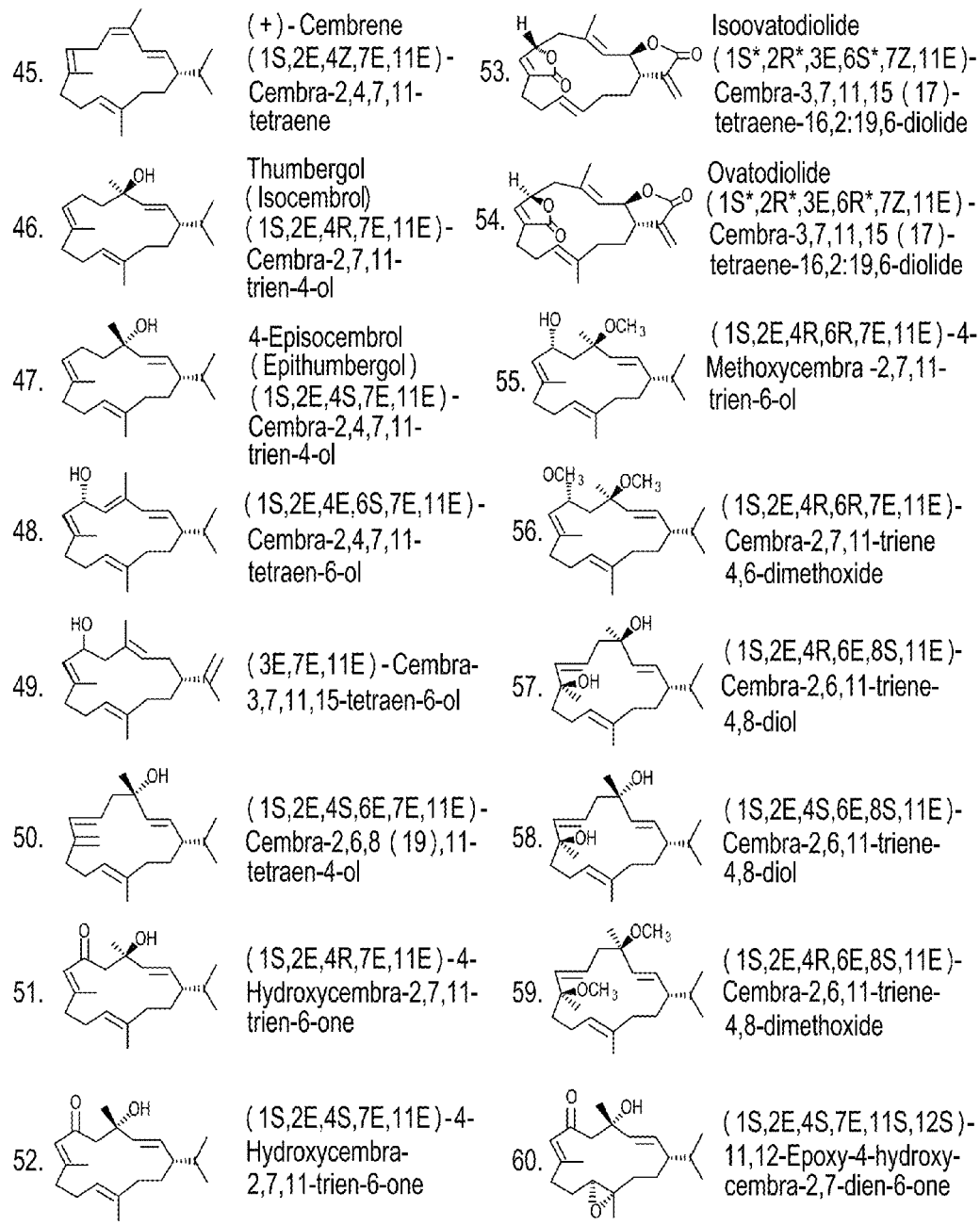
Figure 14:
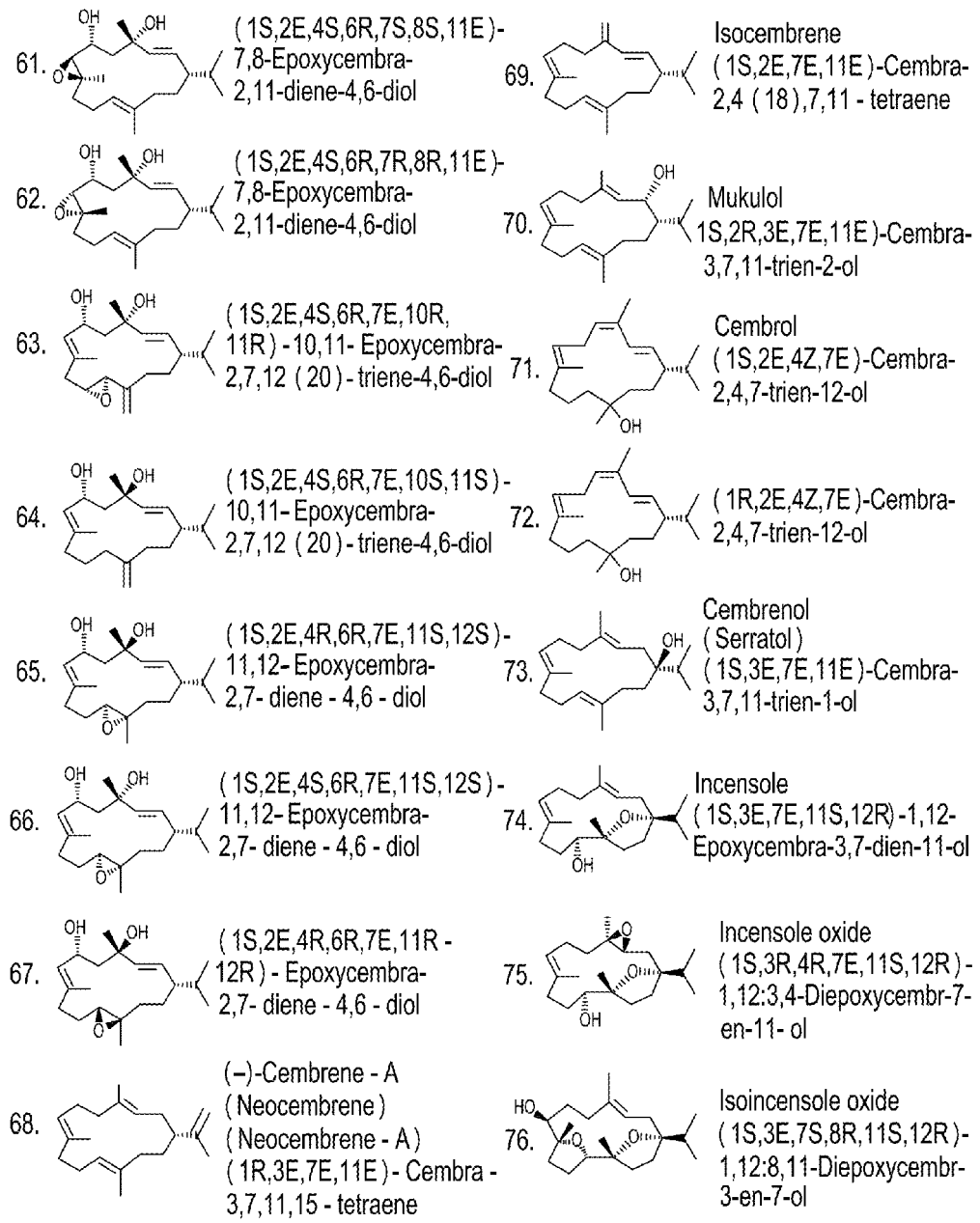
Figure 14:
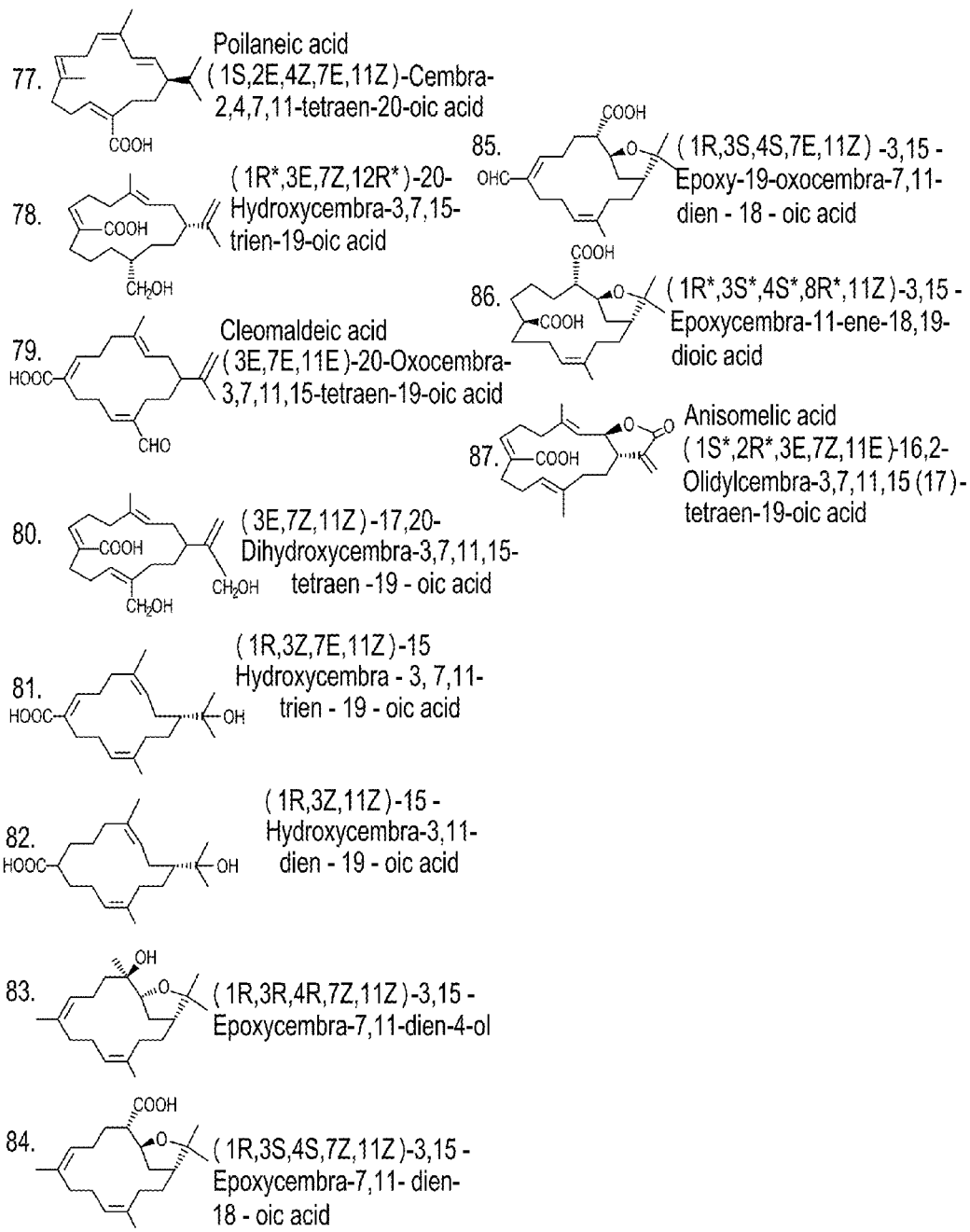

FIG. 14. Enumerated compounds 1-87 of FIG. 14 are diagrams of the chemical structure of macrocyclic diterpenoids.

Figure 15:
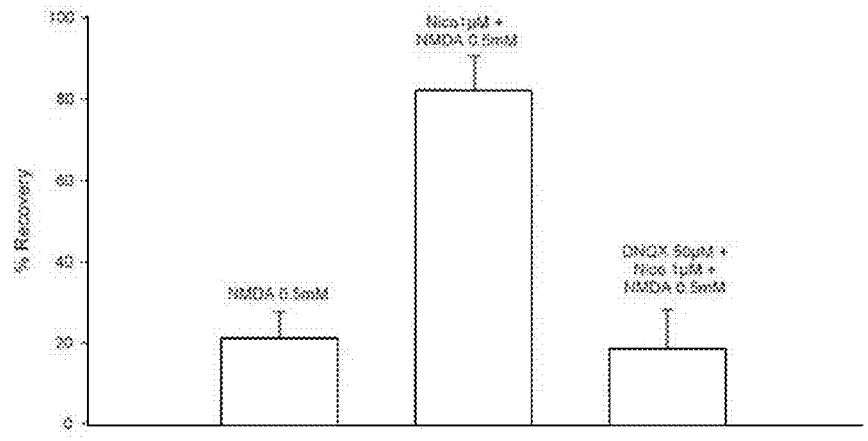

FIG. 15 is a graph showing that acute rat hippocampal slices pretreated with nicotine recovered significantly more electrophysiological activity than hippocampal slices exposed to nicotine in the presence of 6,7-dinitroquinoxaline-2,3-dione (DNQX) or treated only with NMDA. The neuroprotective effect of nicotine depends on the activity of AMPA/kainate-type glutamate receptors (p<0.05, N=21). The NMDA controls were perfused with ACSF for another hour followed by 0.5 mM NMDA for 10 min (1st bar). The second group was perfused with 1 μM nicotine during 1 hr followed by 0.5 mM NMDA (2nd bar). The third group was perfused with 1 μM nicotine during 1 hr in the presence of 50 μM 6,7-dinitroquinoxaline-2,3-dione (DNQX) a selective inhibitor of the AMPA/kainate or non-NMDA glutamate receptors followed by 0.5 mM NMDA (3rd bar).

Figure 16:
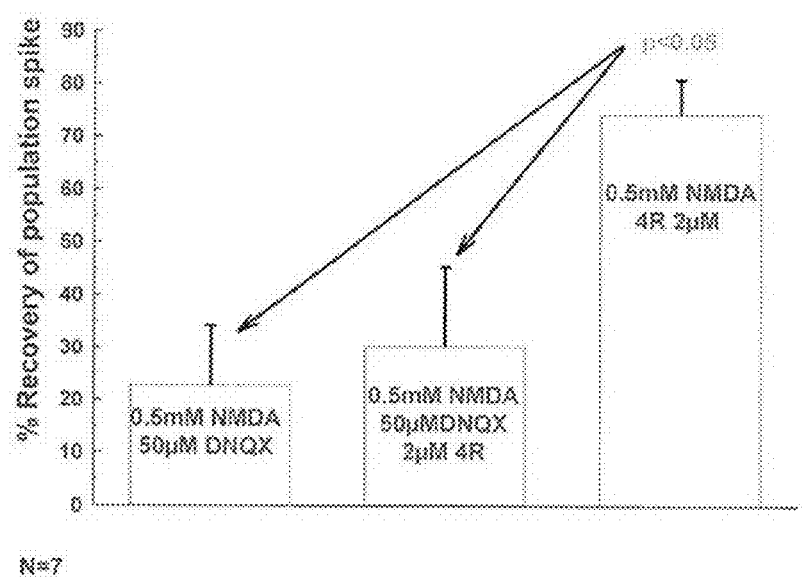

FIG. 16 is a bar graph demonstrating that the neuroprotective effect of 4R is inhibited by DNQX and that the neuroprotective effect of 4R depends on the activity of AMPA/kainate-type glutamate receptors.

Figure 17:
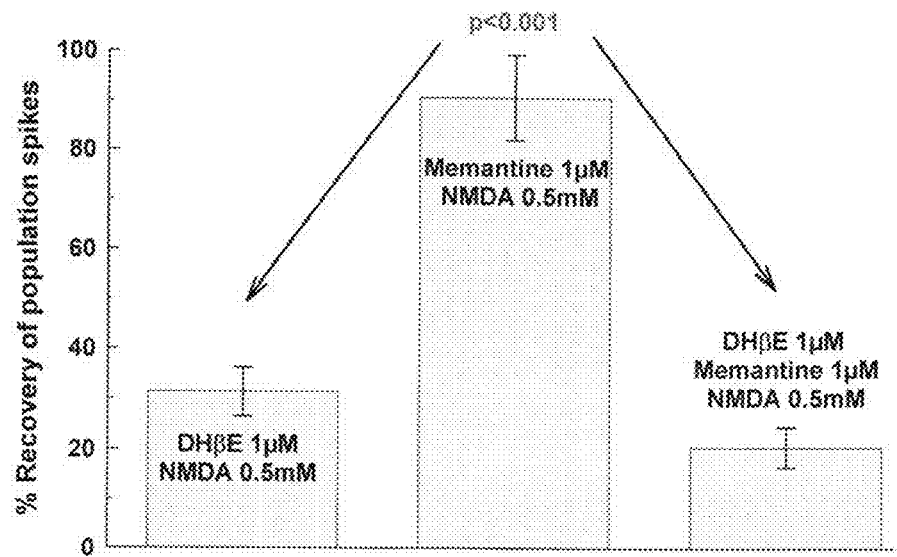

FIG. 17 is a bar graph demonstrating that DHβE inhibits the neuroprotective effect of memantine. The lack of neuroprotection by memantine administered in the presence of DHβE, thus demonstrating a nicotinic mechanism in memantine mediated neuroprotection.

Figure 18:
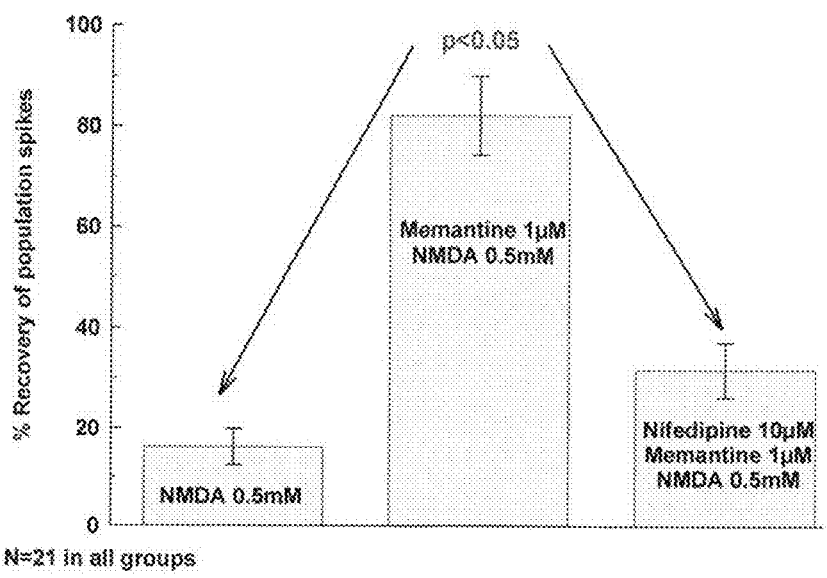

FIG. 18 is a bar graph demonstrating that nifedipine inhibits the neuroprotective effect of memantine. The first bar demonstrates the toxicity of NMDA. The middle bar demonstrates that nifedipine coincubated with memantine abrogates the neuroprotective effects, as would be expected from the mechanism B as depicted in FIG. 12.

Figure 19:
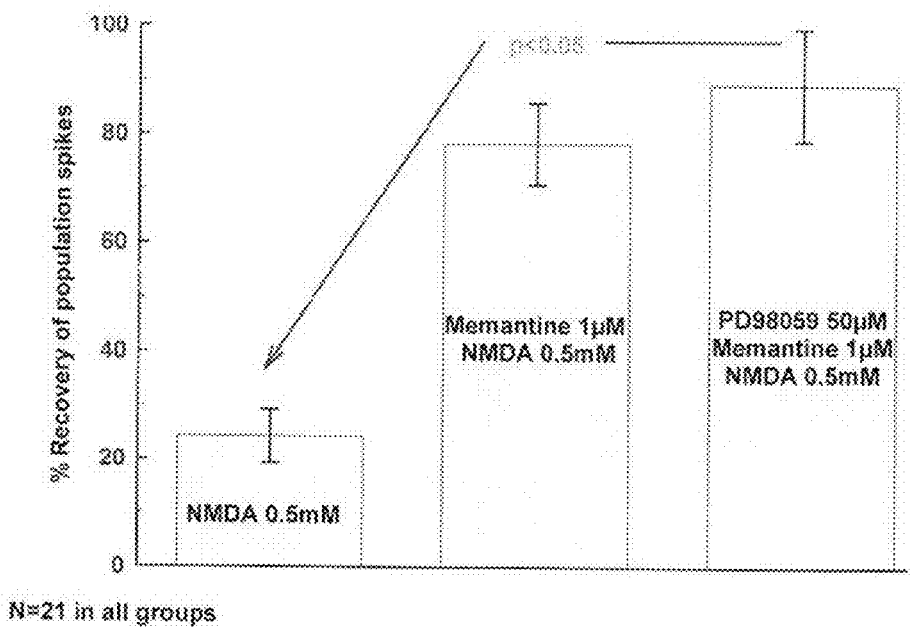

FIG. 19 is a bar graph demonstrating that the effect of memantine is not inhibited by the inhibitor of MAP kinase ERK-1,2 as expected by the mechanism B as depicted in FIG. 12. The first bar demonstrates the toxicity of NMDA. The middle bar demonstrates the neuroprotective effect of memantine. The last bar demonstrates the failure of the inhibitor of activation of the Ras/MEK/ERK cascade by 50 μM PD98059 to inhibit the protection by memantine.

Figure 20A:
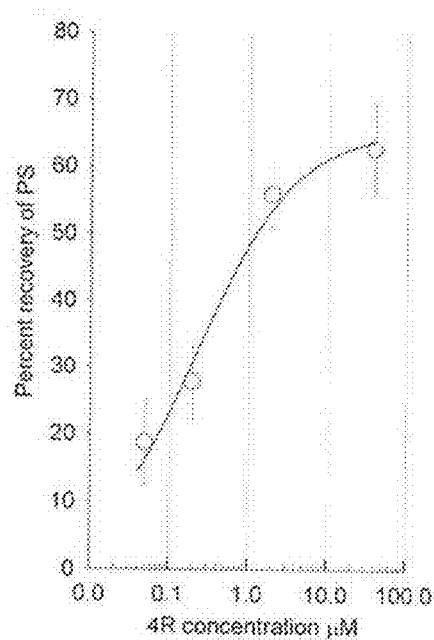
Figure 20B:
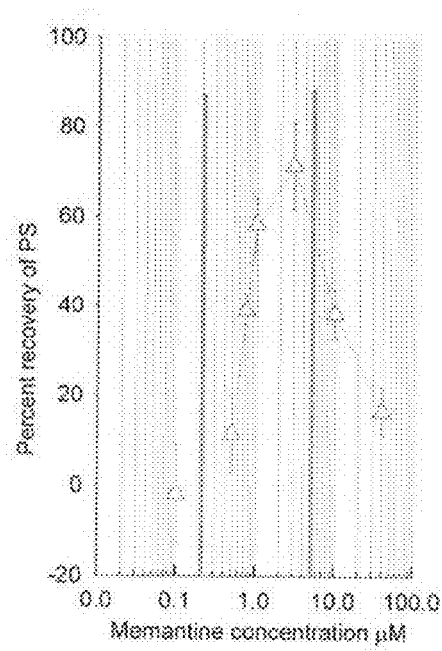

FIGS. 20A-B. These figures represent a comparison of the dose-response curves for the neuroprotective effects of 4R (FIG. 20A) and memantine (FIG. 20B). FIG. 20A illustrates the neuroprotective activity of 4R against its concentration. FIG. 20B illustrates the neuroprotective activity of memantine against its concentration. The two vertical lines of FIG. 20B indicate the $IC_{50}$ of memantine against the α7 nAChRs (left line, $IC_{50=0.34}$ μM) and against the NMDA receptors (right line, $IC_{50=5.1}$ μM), thus demonstrating that memantine starts to neuroprotect at concentrations similar to its $IC_{50}$ for the α7 nAChRs while at concentrations similar to its $IC_{50}$ for the NMDA receptors, memantine blocks its own neuroprotection.

Figure 21:
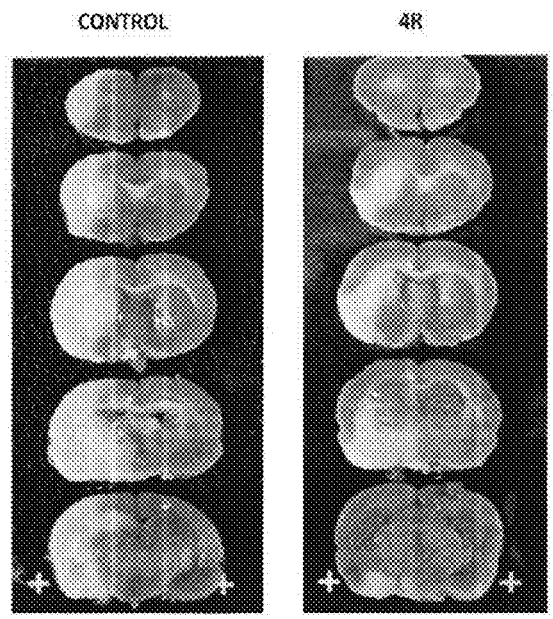

FIG. 21. This figures depicts slices from the brains of rats subjected to permanent middle cerebral artery occlustion (pMCAO). White-colored areas indicate necrotic tissue while darker areas correspond to healthy tissue. Necrotic areas are smaller in rats that received 4R, thus demonstrating that 4R reduces infarct formation following pMCAO.

Figure 22:
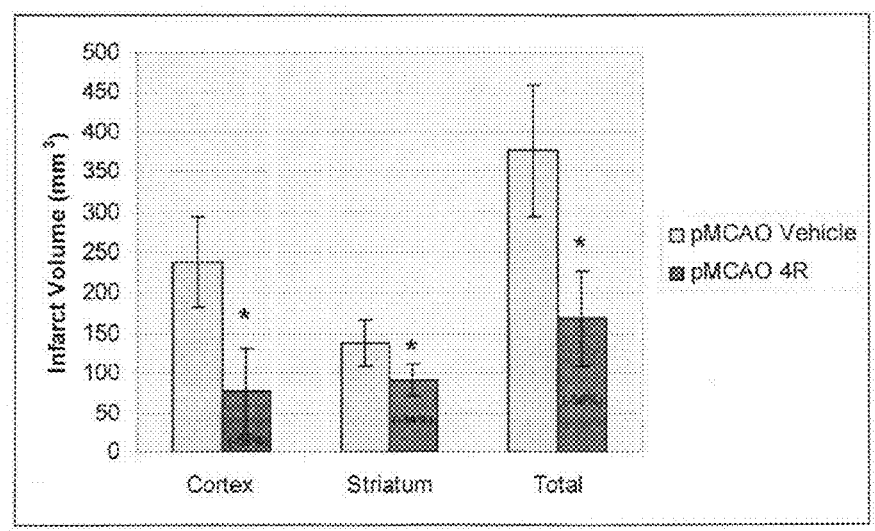

FIG. 22 is a bar graph demonstrating the statistical analysis of the effect of 4R on the brains of rats subjected to pMCAO.

DETAILED DESCRIPTION OF THE INVENTION

Tobacco and cigarette smoke contain many pharmacologically active compounds besides nicotine, including cembranoids (Saito, Y. et al., Carcinogenesis 6:1189-1194 (1985)). Cembranoids are macrocyclic diterpenoids with a fourteen-carbon cembrane ring that are found in terrestrial plants and marine coelenterates (Wahlberg I., et al., Acta Chem Scan B 40:855-860 (1986); Rodriguez A. D., Tetrahedron 51:4571-4618 (1995). The most abundant cembranoids found in tobacco FIGS. 1A and 1B) are (1S,2E,4S,6R,7E,11E)-cembra-2,7,11-triene-4,6-diol (4S) and its isomer (1S,2E,4R,6R,7E,11E)-cembra-2,7,11-triene-4,6-diol (4R) (Wahlberg I., and Eklund, A. M., Prog Chem Org Nat Prod 60:1-141 (1992)). Cembranoids from marine invertebrates are non-competitive inhibitors of Torpedo (Hann. R. M., et al., J Pharmacol Exp Ther 287:253-260 (1998)) and other nicotinic acetylcholine receptors (nAChRs) (Eterovic, V. A., et al., Cell Mol Neurobiol 13:99-110 (1993); Eterovic V. A., et al., Cell Mol Neurobiol 13:111-121 (1993)). This was later extended to tobacco cembranoids by showing that 4R inhibits the function of α3β4 and α4β2 nAChRs with $IC_{50}$ of 2.2 and 19.1 μM, respectively; however, the $IC_{50}$ of cembranoids for α7 has not been determined yet. In addition, 6 mg/kg of 4R decreases the expression of behavioral sensitization to nicotine (Ferchmin, P. A., et al., J Neurosci Res 64:18-25 (2001)).

The possibility of a functional interaction between nicotine and cembranoids is intriguing since tritiated 4R injected into the rat caudal vein was found in the brain suggesting that the interaction between nicotine and cembranoids is of pharmacological and medical interest. Nicotine was found to be neuroprotective in a variety of experimental systems and epidemiological studies (Belluardo, N., et al., Behav Brain Res 113:21-34 (2000); Kaneko S., et al., Brain Res 765:135-140 (1997); Kihara T., et al., J Biol Chem 276:13541-13546 (2001); Maggio R., et al., J Neural Transm 104:1113-1123 (1997); Marin P., et al., Neuroreport 5:1977-1980 (1994); Ross G. W., and Petrovitch, H., Drugs Aging 18:797-806 (2001)). Since nicotine, a nicotinic agonist, is neuroprotective, it could be concluded that cembranoids, which are antagonists, would diminish nicotinic neuroprotection. However, methyllycaconitine (MLA), an α7 antagonist, has been reported to be neuroprotective (Ferchmin P. A., et al., J Pharmacol Exp Ther 305:1071-1078 (2003)) and a neuroprotective effect of MLA was reported for neonatal mice (Laudenbach V., et al., FASEB J 16:423-425 (2002)). Similarly, it was found that 4R is neuroprotective.

Nicotine via nAChRs activates protein kinases that mediate neuroprotection (Dajas-Bailador, F. A., et al., J Neurochem 80:520-530 (2002); Ferchmin P. A., et al., J Pharmacol Exp Ther 305:1071-1078 (2003); Kihara T., et al., J Biol Chem 276:13541-13546 (2001)) and it is likely that 4R acts through similar kinases. The activation of Raf/MEK-1,2/extracellular signal regulated kinase (ERK)-1,2 and phosphatidylinositol-3 kinase (PI3K)/Akt pathways favors neuronal survival and the relative contribution of each pathway depends, among other things, on the specific type of cellular injury (Hetman, M., et al., J Biol Chem 277:49577-49584 (2002)). A balance between prosurvival and apoptotic signals determines the function and survival of neurons. Glycogen synthase kinase-3β (GSK3) is involved in neuronal apoptosis. PI3K indirectly activates Akt by phosphorylation of Ser473 and Thr308. Activated Akt inactivates GSK3-β by phosphorylation of Ser9 or Ser21 in the case of the isoform GSK3-α (Datta S. R., et al., Genes Dev 13:2905-2927 (1999); Hetman, M., et al., J Biol Chem 277:49577-49584 (2002)). The roles of these kinases in neuroprotection by 4R and nicotine were compared.

The area of the population spike (PS) is proportional to the number of functional pyramidal neurons capable of producing action potentials (Andersen P., et al., Exp Brain Res 13:208-221 (1971)). Excitotoxicity, therefore is defined here as PS decrease by N-methyl D-aspartate (NMDA) treatment and neuroprotection as increased recovery after NMDA mediated by ligands of nAChRs. The measurement of PSs to assess the degree of excitotoxic damage is known in the art. This method measures the early neuroprotective effect; however, the protective cell signaling pathways described are similar to those reported for neuronal survival. Additionally, NMDA induces apoptosis and antiapoptotic treatment prevents the loss of PS suggesting that nicotine and 4R block synaptic apoptosis which leads to neuronal death (Mattson M. P., Brain Pathol 10:300-312 (2000); Mattson, M. P., et al., Biochem Soc Symp 67:151-162 (2001).

4R provided a robust neuroprotection of the physiological activity of CA1 neurons against NMDA; however, 4R did not block the NMDA receptors or produce any spurious artifacts that could explain the increased recovery of PSs after NMDA treatment (FIGS. 3A-1, 3B-1 and 3C-1). Both 4R and 4S (FIGS. 1A and 1B) isomers were active but there was a significant difference in the extent of neuroprotection caused by each of them (Bar Graph B of FIG. 5). The apparent higher activity of 4R versus 4S on nicotinic receptors was observed previously in a different experimental system (Ferchmin, P. A., et al., J Neurosci Res 64:18-25 (2001)).

A neuroprotective cell signaling cascade is involved in 4R-mediated neuroprotection because this cembranoid does not block NMDA receptor potentials; it is effective when applied either before or after NMDA (Bar Graph C of FIG. 5) and extracellular $Ca^{2+}$ is necessary to effect neuroprotection (Bar Graph D of FIG. 5). The neuroprotection by 4R applied after NMDA is not surprising since this compound initiates a neuroprotective program. A similar post-injury neuroprotection has been described for nicotine by Ferchmin et al. (J Pharmacol Exp Ther 305:1071-1078 (2003)) and by others (Dajas-Bailador, F. A., et al., Neuropharmacology 39:2799-2807 (2000)). Although an overload of $Ca^{2+}$ is a hallmark of excitotoxic damage, the crucial factor is not only the total $Ca^{2+}$ concentration because the route of $Ca^{2+}$ entry is critical in determining which signaling pathway will be activated (Hardingham, G. E., and Bading, H., Trends Neurosci 26:81-89 (2003)). In dissociated neuronal cultures, nicotine increases intracellular $Ca^{2+}$ and activates a cell-signaling pathway that leads to neuronal survival (Dajas-Bailador, F. A., et al., Neuropharmacology 39:2799-2807 (2000)).

Neuroprotection mediated by 4R (Bar Graph E of FIG. 5) as well as by nicotine (Ferchmin P. A., et al., J Pharmacol Exp Ther 305:1071-1078 (2003)) was blocked by 1 μM DHβE, suggesting a dependence on the activity of the α4β2 nAChR in both cases. In hippocampal area CA1, 10 μM DHβE specifically inhibits the slow ACh evoked currents mediated by α4β2, sparing other nicotinic currents (Alkondon, M., et al., J Pharmacol Exp Ther 283:1396-1411 (1997)). Raggenbass and Bertrand (J Neurobiol 53:580-589 (2002)) narrowed to >1 µM the range of selectivity of DHβE for α4β2. More recently, the functional $IC_{50}$ of DHβE for human α4β2 nAChRs was reported to be 1.5 µM (Eaton, J. B., et al., Mol Pharmacol 64:1283-1294 (2003)). In a comprehensive review about the pharmacology of nAChRs, it is reported that the Ki values of DHβE for α4β2, α3β4, and α7 are 0.014-1.9 µM, 218 µM, and 25-57 µM, respectively (Sharples C. G. and Wonnacott, S., Tocris Rev 19:1-12 (2001)). In conclusion, 1 µM DHβE is about 200-fold lower than the $IC_{50}$ for α3β4 and 20-fold lower than the $IC_{50}$ for α7. Therefore, 1 µM DHβE selectively inhibits the α4β2 receptor.

Although 4R blocks α4β2 nAChR with an $IC_{50}$ of 19.1 µM (Ferchmin, P. A., et al., J Neurosci Res 64:18-25 (2001)), its neuroprotective effect was significant from 0.2 to 40 µM with an apparent $EC_{50}$ of 0.24.+−0.0.12 µM (FIG. 6). It is therefore unlikely that 4R acts directly on the α4β2 nAChR. This is supported by the finding that tobacco cembranoids block the α7 receptor with higher affinity than does the heteromeric receptors expressed in PC12 cells. In agreement with these results, neuroprotection by 10 nM MLA, a selective al antagonist (Radcliffe K. A., et al., Ann N Y Acad Sci 868: 591-610 (1999); Alkondon M., and Albuquerque, E. X., J Neurophysiol 56:3043-3055 (2001)), was also blocked by 1 µM DHβE (Ferchmin P. A., et al., J Pharmacol Exp Ther 305:1071-1078 (2003)).

The present and previously reported data indicate that nicotine, an agonist, MLA, an α7 antagonist, and 4R, a less-studied α7 antagonist, all protect against NMDA neurotoxicity in the presence of active α4β2 receptors. This can be explained by the fact that nicotine can directly stimulate α4β2 receptors whereas MLA and other α7 inhibitors could-indirectly activate α4β2 receptors by enhancing synaptic acetylcholine (ACh) release. MLA inhibits α7 receptors on .gamma.-aminobutyric acid (GABA)ergic interneurons and decreases synaptic GABA release (Alkondon M., and Albuquerque, E. X., J Neurophysiol 56:3043-3055 (2001)). Furthermore, inhibition of GABAergic activity increases the release of ACh (Materi, L. M., and Semba K., Eur J Neurosci 74:38-46 (2001)), which activates the α4β2 nAChRs, increases glutamate release which activates the NMDA receptor and induces neuroprotection (see FIG. 11).

A series of selective cell-signaling inhibitors was used to explore the events downstream from the interaction of 4R or nicotine with the nAChRs. Only inhibitors that neither affected the field potentials nor exacerbated the toxicity of NMDA were used. Three of the inhibitors used, PD98059, Ro-31-8220, and nifedipine, differentially affected the neuroprotection by 4R and nicotine. PD98059, a MEK-1,2 inhibitor, was tested on the neuroprotection mediated by 4R and nicotine. The neuroprotection by 4R was not affected (Bar Graphs F and G, FIG. 5) but that of nicotine was inhibited robustly (Bar Graph G of FIG. 5). Similarly, Ro 31-8220, a broad-spectrum PKC inhibitor, did not decrease the neuroprotection by 4R (Bar Graph H of FIG. 5) but inhibited the effect of nicotine (Bar Graph I of FIG. 5). Neither nifedipine nor the CaM kinase inhibitor KN-62 inhibited the neuroprotection by nicotine (Ferchmin P. A., et al., J Pharmacol Exp Ther J05:1071-1078 (2003)). Here, the effect of nifedipine and KN-62 on the neuroprotection by 4R and nicotine were compared (FIG. 7). Contrary to nicotine-mediated neuroprotection, the neuroprotection by 4R was inhibited by nifedipine and to a lesser extent by KN-62. Thus, different mechanisms are involved in the protective effect of 4R and nicotine.

The remaining inhibitors did not differentially affect the neuroprotection by 4R and nicotine. The PKA inhibitor, KT5720, partially but significantly decreased the effect of nicotine and 4R (Bar Graphs C and D, FIG. 7). Using the same concentration of KT5720 (0.5 µM) Dajas-Bailador, et al. (J Neurochem 50:520-530 (2002)) have shown inhibition of the nicotine evoked ERK-1,2 activity enhancement.

The activation of Akt by PI3K is one of the most frequent steps involved in neuroprotection (Hetman, M. and Xia, Z. Acta Neurobiol Exp (Wars) 60:531-545 (2000)). Consistent with that, PI3K activity was needed for neuroprotection mediated by 4R (Bar Graphs E and F, FIG. 7) and by nicotine (Ferchmin P. A., et al., J Pharmacol Exp Ther 305:1071-1078 (2003)). The nature of the inhibitors that prevent the neuroprotective effect of 4R and nicotine suggests that NMDA initiates early apoptotic steps reflected in the loss of the PSs. This is supported further by the finding that SB216763, an inhibitor of GSK3 (Carmichael, J., et al., J Biol Chem 277: 33791-33798 (2002)), was able to stop the excitotoxic events after NMDA administration but not prevent it by application before NMDA (Bar Graph G, FIG. 7).

To confirm the data obtained with inhibitors, the effect of 4R on the activation by phosphorylation of ERK-1,2 and Akt and on the inhibition by phosphorylation of GSK3 was studied with Western blots. During the first 30 min of 4R application, the activation of Akt by phosphorylation was enhanced but there was no significant phosphorylation of ERK-1,2 (FIG. 9). This agrees with the finding that inhibition of ERK-1,2 phosphorylation with 50 µM PD98059 did not inhibit 4R neuroprotection (Bar Graph F of FIG. 5); however, inhibition of PI3K, a kinase that phosphorylates Akt did inhibit neuroprotection (Bar Graphs E and F, FIG. 7).

4R-mediated neuroprotection, was inhibited by 1 µM DHβE (Bar Graph E of FIG. 5); this was reflected in the inhibition by DHβE of 4R-mediated phosphorylation of Akt, but not in the basal Akt phosphorylation (FIG. 10). DHβE per se did not alter the recovery of PSs with or without NMDA.

The 4R-mediated activation by phosphorylation of Akt and the inactivation by phosphorylation of the proapoptotic GSK3 shows a dose-dependent increase that contrasts with the lack of effect on ERK-1,2 phosphorylation (FIG. 11). The phosphorylation of ERK-1,2 was not increased by 4R up to 40 µM. Akt phosphorylation was increased at higher 4R doses following the pattern of the dependence of neuroprotection on 4R concentration (FIG. 6). The phosphorylation of the inhibitory site of GSK3 increased markedly at 4R concentrations higher than 10 µM. To avoid the possible confounding effects of small nonsignificant increases in total ERK-1,2 after 4R treatment, the absolute increase in phosphoenzymes relative to total proteins was used in this work instead of the ordinarily used ratio of phospho- to total enzyme. The total levels of phosphoenzyme provide a measure of the activity of ERK-1,2 and Akt or inactivity of GSK3.

Nicotine and 4R neuroprotect by two different DHβE-sensitive mechanisms. As mentioned before, PD98059 and Ro 31-8220 did not inhibit the neuroprotection by 4R but did inhibit the neuroprotection by nicotine (Bar Graphs F-I, FIG. 5). On the contrary, nifedipine inhibited the neuroprotection by 4R but not by nicotine (Bar Graph A, FIG. 7). The sensitivity of both neuroprotective pathways to 1 µM DHβE shown in Bar Graph E of FIG. 5 for 4R and reported previously for nicotine (Ferchmin P. A., et al., J Pharmacol Exp Ther 305: 1071-1078 (2003)) demonstrates that α4β2 receptors are involved in both cases.

Based on data and observations presented herein, it has been determined that there are two distinct, but co-existing, models of neuroprotective pathways mediated by α4β2 nicotinic receptors. In one pathway, nicotine directly activates the α4β2 nicotinic receptors located on the presynapses of glutamatergic neurons, thus increasing glutamate release and consequently increasing the activation of the postsynaptic glutamate receptors of the non-NMDA type; Ca2+ entry through these receptors activates the cell-signaling pathway A. In the alternative pathway, the α4β2 nicotinic receptors are indirectly activated. For example, 4R (or MLA, or memantine) inhibits the α7 receptor on GABAergic terminals, thus decreasing the release of GABA from interneurons. The decreased GABAergic inhibition on cholinergic terminals increases acetylcholine release and increases synaptic stimulation of a subsynaptic pool of α4β2 receptors, which increases the release of glutamate, which activates AMPA and NMDA receptors located on pyramidal (principal) neurons. The consequent local depolarization activates voltage-gated calcium channels (VGCC) $Ca^{2+}$ entering through VGCC and through glutamate receptors triggers cell-signaling pathway. Akt is activated by Ca2+ and Akt activates CREB, inhibits the proapoptotic GSK-3, and inhibits mitochondria dependent apoptosis, resulting in neuroprotection. (FIG. 12).

Nicotinic modulation through the α4β2 receptors protects the capability of CA1 neurons to produce PSs against NMDA toxicity by activation of two different protective cell-signaling pathways. The data may also be relevant to a major health problem: smoking Tobacco contains nicotine that mediates one pathway and cembranoids that are shown here to mediate another neuroprotective pathway, rather than antagonizing the neuroprotective effect of nicotine.

One embodiment of Applicants' invention is a novel method for inhibiting apoptosis in a neuron in its native environment, e.g. in ex vivo experiments as described herein Inhibition of apoptosis can be accomplished by exposing a neuron in its native environment, e.g. in hippocampi slices prepared as described herein, with at least one macrocyclic diterpenoid, in particular, a tobacco cembranoid or a biologically active fragment, analog, or derivative thereof. The term "biologically active material" as used throughout the specification and claims means a compound or composition which, when present in an effective amount, reacts with and/or affects living cells and organisms.

Another embodiment of Applicants' invention is a novel method of inhibiting excitotoxicity in a mammal by, administering to the mammal at least one macrocyclic diterpenoid, such as 4R or a biologically active fragment, analog, or derivative thereof.

Another embodiment of Applicants' invention is a novel method of treating or preventing neuronal damage in a subject by administering to the subject at least one macrocyclic diterpenoid, for example, a tobacco cembranoid, or a biologically active fragment, analog, or derivative thereof.

This method of treating or preventing neuronal damage can be used as the basis for development of therapeutics against neurodegenerative diseases, including, but not limited to, Alzheimer's Disease, Parkinson Disease, Frontotemporal Dementia, Amyotrophic Lateral Sclerosis (ALS), Motor Neuron Disease, the delayed effects of stroke, the delayed effects of traumatic brain injury, and AIDS related dementia. It can also be used as the basis for development of therapeutics against diseases associated with neuronal impairment, including, but not limited to, glaucoma caused by optical nerve damage, delayed effects of epilepsy, and multiple sclerosis.

Macrocyclic diterpenoids such as those shown in FIG. 14, including, but not limited to, cembranoids of marine and terrestrial origin and other inhibitors of α7 nAChRs, such as MLA, that avoid neuronal apoptosis by acting through the described physiological mechanism can be used to treat or prevent neurodegenerative diseases, including, but not limited to, Alzheimer's Disease, Parkinson Disease, Frontotemporal Dementia, Amyotrophic Lateral Sclerosis (ALS), Motor Neuron Disease, the delayed effects of stroke, the delayed effects of traumatic brain injury, and AIDS related dementia. Such compounds can also be used to treat or prevent diseases associated with neuronal impairment, including, but not limited to, glaucoma caused by optical nerve damage, delayed effects of epilepsy, and multiple sclerosis. Any such compounds used to treat or prevent neurodegenerative diseases or diseases associated with neuronal impairment can be tested for neuroprotective effectiveness by the methods described herein.

The dosage regimen utilizing the compounds disclosed herein can be selected in accordance with a variety of factors including age, weight and sex of the subject being treated; the disease being treated; the severity of the condition to be treated; the route of administration; the renal and hepatic function of the subject; and the particular compound or salt thereof employed. The skilled artisan can readily determine and prescribe the effective amount of at least one macrocyclic diterpenoids required to treat, for example, to prevent, inhibit (fully or partially) or arrest the progress of a neurodegenerative disease or a disease associated with neuronal impairment.

It is understood that the total dosage amount per day can be administered in a single dose or can be administered in multiple dosings such as twice, three or four times per day. The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The compounds herein described can also be administered in conjunction with other currently used drugs to augment or supplement their therapeutic effects.

The therapeutic agents can be formed into dosage unit forms, such as for example, creams, ointments, lotions, powders, liquids, tablets, capsules, suppositories, sprays, aerosols or the like. If the therapeutic agent is formulated into a dosage unit form, the dosage unit form may contain an effective amount of active agent to affect neuroprotection. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant(s), lubricant(s), plasticizer(s), colorant(s), dosage vehicle(s), absorption enhancer(s), stabilizer(s), or the like.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

The compositions used in the methods of the present invention can be formulated as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods of the instant invention, and mixtures comprising two or more of such compounds, pharmaceutically acceptable salt's of the compounds and pharmaceutically acceptable solvates of the compounds. Such compositions are prepared in accordance with acceptable pharmaceutical procedures such as described in Remington's Pharmaceutical Sciences, 17th edition, ed. Alfonso R. Gennaro, Mack Publishing Company, Eaton, Pa. (1985).

The term "pharmaceutically acceptable salt" refers to salt forms that are pharmacologically suitable for or compatible with the treatment of patients, in particular, humans. If the compound used in the methods of the invention is a base, the desired pharmaceutically acceptable salt may be prepared by a suitable method available in the art, for example, treatment of the free base with an inorganic acid, such as hydrochloric acid, hydrobromic acid, sulfuric acid, nitric acid, phosphoric acid (e.g. the hydrochloride, hydrobromide, sulfate, nitrate, phosphate, salts etc.); and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, (e.g. the acetate, maleate, formate, trifluoroacetate, tartrate, methanesulfonate, benzenesulfonate, p-toluenesulfonate, salts etc.) or the like.

If the compound used in any of the methods of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of the suitable salts include organic salts derived from amino acids, such as glycine and arginine, ammonia, primary, secondary, and tertiary-amines, and cyclic amines, such as piperidine, morpholine and piperazine, and inorganic salts derived from sodium, calcium, potassium, magnesium, manganese, iron, copper, zinc, aluminum and lithium.

The term "solvate" as used herein means a compound used in the methods of the invention, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate".

EXAMPLES

The invention is further described in the following examples that are in no way intended to limit the scope of the invention.

Example 1

Slice Preparation and Electrophysiological Recordings

Male Sprague-Dawley rats (120-200 g) were maintained and sacrificed according to standard procedures reviewed and approved by the Institutional Animal Care and Use Committee. The ex vivo methods for the dissection of hippocampi and the preparation of slices have been described previously (Ferchmin P. A., et al., J Pharmacol Exp Ther 505:1071-1078 (2003)). Briefly, hippocampi were dissected over ice; transversal 400-μm-thick slices were cut with a manual slicer and immediately transferred to the incubation chamber, thus preserving the neurons in their native environment. The chamber consisted of a temperature-controlled bath surrounding an acrylic plate covered with nylon mesh; the plate was divided into three lanes with independent perfusion. For dissection and incubation, a standard artificial-cerebrospinal fluid (ACSF) saturated with 95% $O_2$, 5% $CO_2$ was used and contained (in mM): 125 NaCl, 3.3 KCl, 1.25 $NaH_2PO_4$, 2 $MgSO_4$, 2 $CaCl_2$, 25 $NaHCO_3$, and 10 glucose. The slices were kept in the lanes over the mesh, at the interface between ACSF and warmed and humidified 95% $O_2$, 5% $CO_2$ at 34.+−.1.degree. C. A bipolar electrode placed in the stratum radiatum was used to stimulate the Shaffer collateral incoming fibers with a constant current for 0.2 msec. The resulting population spike (PS) was recorded in stratum pyramidale with a glass electrode filled with 2 M NaCl, having an impedance of 1-5 M.OMEGA.

For immunoassays of phosphorylated proteins, in the initial experiments slices were incubated in the same conditions as for PS determination. Later, the slices were incubated by being submerged in a static chamber on culture insets (Millicell; Millipore, Billerica, Mass.) to avoid drying during timed removal of slices. There was no difference in the results obtained from either method.

Example 2

Procedure for Testing Neurotoxicity and Neuroprotection

About 30 slices from the hippocampi of two rats were distributed equally among three lanes of an incubation chamber. A maximum of seven slices were analyzed per lane for each individual experiment, and on average 21 slices per condition were tested for each experimental condition. The excitotoxic stimulus was 0.5 mM NMDA for 10 min in the presence of 95% C % 5% $CO_2$, and 10 mM glucose. Because the neurons are maintained in their native environment and in contact with other cells, stimulation with the appropriate stimulus can elicit a PS. One hour after dissection, each slice was stimulated with a stimulus twice the strength required to elicit a threshold PS. This initial response was recorded as PS area (msec×mV) and compared to the final response elicited by the same stimulus strength recorded from the same position after the experimental treatment was finished. The slices were washed for 1 hr with normal ACSF to eliminate lingering drugs and any short-lived effects. The concentration and length of exposure to NMDA were chosen to recover an average of 20% of the PS area after NMDA treatment (Ferchmin P. A., et al., Brain Res 859:273-219, (2000)). The percentage of the initial response remaining at the end of the experiment was used as a measure of electrophysiological recovery.

FIG. 2 shows a sketch of the experimental design of a typical experiment in which a, slice is pretreated with an inhibitor of the effect of 4R, and then treated with 4R plus the inhibitor followed by the application of NMDA.

The protective effect of 4R was tested at 0.05, 0.2, 2, 10, 20, and 40 μM. A significant protection was achieved with 0.2 μM (200 nM) 4R (P<0.05; Kruskal-Wallis ANOVA on ranks) Further increase in 4R concentration enhanced neuroprotection (FIG. 6). All 4R-treated groups pooled together differed significantly from control slices treated only with NMDA (P<0.001).

DMSO was used routinely to dissolve tobacco cembranoids and other hydrophobic inhibitors; therefore, DMSO was added at the same final concentration in all experimental groups in a given experiment. At the concentrations used (<0.1% vol/vol), DMSO had no effect on the recovery of PSs. Marine cembranoids, structurally related to tobacco cembranoids, were extensively tested on field potentials recorded in area CA1 and no effect was found. In addition, 4R was tested and no direct effects on field potentials were detected. All inhibitors used in these experiments were tested for effects on the size or shape of the PSs and on NMDA toxicity; inhibitors that affected the field potentials were not used.

Example 3

Western Blotting Analysis

Slices were prepared and maintained as described above. Treatments started after 2 hr of incubation in ACSF. The tobacco cembranoid 4R, dissolved in DMSO, was applied as needed for each experimental condition. At the corresponding time, each slice was removed and the CA1 region microdissected, frozen on dry ice, and stored at −80.degree. C. until assayed. Control slices not exposed to 4R were incubated in ACSF with the same concentration of DMSO as experimental slices. The CA1 regions were sonicated briefly in ice-cold homogenization buffer (pH 7.0) containing: (in mM) 20 HEPES, 2 dithiothreitol (DTT), 10 $MgCl_2$, 0.2 PMSF, 15 sodium pyrophosphate, 2 sodium orthovanadate, 5 sodium metavanadate, 50 NaF, and 0.1 mg/ml bovine serum albumin (BSA) with an additional mixture of peptide inhibitors (leupeptin, antipain, bestatin, chymostatin, and pepstatin each at a final concentration of 1.6 μg/ml). An appropriate volume of Laemmli sample buffer with 2-mercaptoethanol was added to the homogenate (for a final concentration of 1 μg protein/μl), and the samples were incubated in a water bath at 100.degree. C. for 6 min. Samples were loaded (8 μl/lane) onto 15% SDS-polyacrylamide gels (Protean Mini-Gel System; Bio-Rad, Hercules, Calif.), and run for 1 hr (200V constant). The proteins were transferred with a semidry transfer cell (Bio-Rad) over night at 4.degree. C. and immediately stained with India ink. After transfer, the membranes were blocked with 5% fat-free milk in 10 mM Tris 100 mM NaCl, and 0.1% Tween 20 (TBST; pH 7.5) for 1 hr. The membranes were washed three times for 15 min with TBST and incubated with corresponding primary antibody overnight at 4.degree. C., followed by three additional washes with TBST for 15 min and incubation with anti-rabbit secondary antibody for 1 hr. Final detection was carried out with enhance chemiluminescence methodology (Pierce Supersignal West Dura) and the intensity of the signal measured in a gel documentation system (Versa Doc Model 1000; Bio-Rad). In all cases, intensity of the chemiluminescence signal was corrected for minor changes in protein content after densitometry analysis of the India ink-stained membrane. In initial experiments treatment with nicotinic drugs induced a small upregulation of total ERK-1,2. Normalization of the signal of the phosphokinase to the total amount of proteins, measured by densitometry of the stained membrane, was used as the relevant parameter, which was the level of activity of the kinase. This method was validated with several isolated cells and tissues and determined a linear relationship between the amount of total protein (as measured by densitometry) and total kinases (as measured by chemiluminescence) within the range of proteins employed in these experiments (4-12 μg total protein). The two methods produce the same results under conditions where no significant change in the total amount of the relevant enzyme is observed. Final values of phosphoenzymes are expressed as percent of control and represent the average of three or more experiments.

Example 4

Data Analysis

The areas of PSs (mV/msec) were acquired and analyzed with the Labman program. The data were statistically analyzed with SigmaStat v2.03 (SPSS, Chicago, Ill.). One-way analysis of variance (ANOVA) was used whenever the data were distributed normally. In some experiments, a large proportion of slices treated with NMDA had zero recovery and the data failed the normality test. In these cases, the less powerful nonparametric Kruskal-Wallis one-way ANOVA on ranks was used. The post-hoc test used was the Student-Newman-Keuls test for normally distributed data and Dunn's test for data that was not normally distributed.

Example 5

Figures 1, 3A:
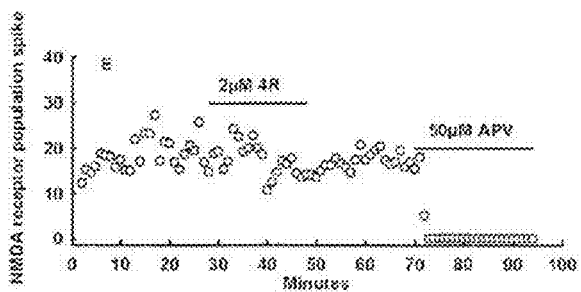
Figures 2, 3A:
FIG. 2 is a graph showing a time course of a typical experiment in which hippocampi slices from male Sprague-Dawley rats recover from dissection (A), the initial population spikes (PSs) are determined during the next hour or 45 min (B), an inhibitor of 4R effect is applied alone for 15 min followed by 1 hr in the presence of 4R (C), 0.5 mM NMDA is applied for 10 min (D), NMDA is removed by washing with normal ACSF for 1 hr during which the slices either recover most of the PS or mostly fail to recover (E), and final PSs are determined (F). This design or variations of it were used throughout studies described in this application.
FIGS. 3A-3C. These figures depict graphs showing that 4R does not affect pharmacologically isolated NMDA receptor-mediated potentials or total field potentials in CA1.
Figures 1, 3B:
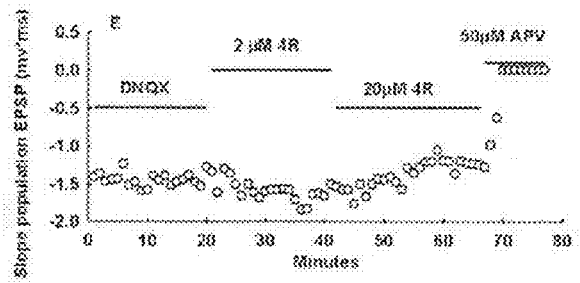
Figures 2, 3B:
Figures 1, 3C:
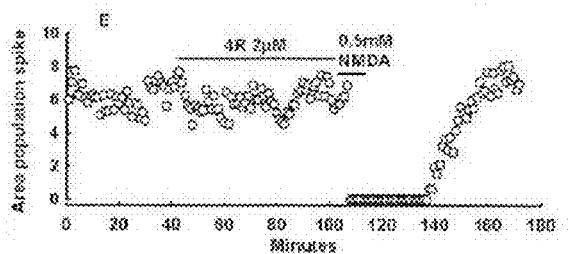
Figures 2, 3C:
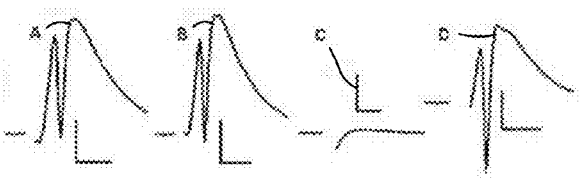
Figure 4:
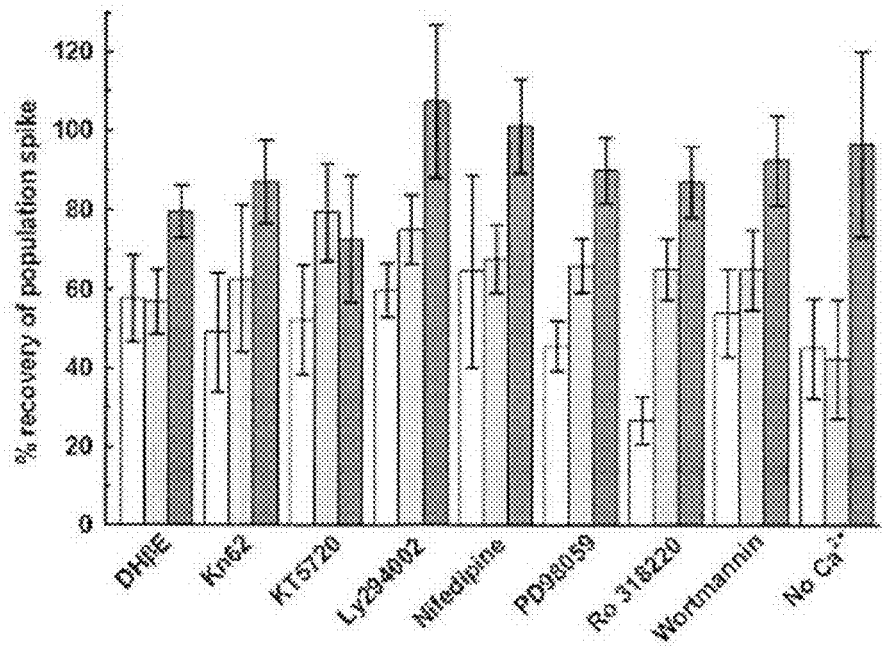
FIG. 4 is a bar graph showing inhibitors and Ca$^{2+}$-free ACSF did not exacerbate the toxic effect of 0.2 mM NMDA. The lower, less toxic, concentration of NMDA was used to allow for detection of either positive or negative effects of inhibitors. All slices were perfused with ACSF for 1 hr before the initial population spikes (PSs) were recorded. There were three experimental conditions in each case. For the NMDA controls, the perfusion with ACSF continued for 1 hr; afterwards 0.2 mM NMDA was applied for 10 min (white bars). The second group was perfused with the inhibitor tested during 1 hr followed by 0.2 mM NMDA for 10 min (light gray bars). The third lane was perfused only with the corresponding inhibitor for 1 hr and no NMDA was applied (dark gray bars). The slices were washed with normal ACSF for more than 1 hr and the final PSs were determined. The concentrations of inhibitors and the number of slices tested, shown in parenthesis, were as follows: 1 μM DHβE (14), 9 μM Kn62 (7), 0.5 μM KT5720 (7), 10 μM LY294002 (14), 10 μM nifedipine (7), 50 μM PD98059 (21), 100 nM Ro 318220 (14), 3 μM SU6656 (7), 10 nM wortmannin (14), and Ca$^{2+}$ depletion (7).

4R does not Protect by Inhibiting the NMDA Receptor and the Inhibitors Used in these Studies do not Exacerbate NMDA Toxicity 4R does not protect against NMDA by blocking NMDA receptors (FIG. 3A-1). DHβE, all the inhibitors of regulatory kinases, nifedipine, and $Ca^{2+}$ removal in the presence of 0.2 mM NMDA were tested to rule out any possible enhancement of NMDA toxicity in the experimental conditions. This reduced concentration of NMDA produces partial excitotoxicity, thus allowing for the detection of exacerbation of NMDA toxicity (Ferchmin P. A., et al., Brain Res 859:273-219, (2000)). No inhibitor or treatment exacerbated the toxicity of NMDA (FIG. 4).

Example 6

Neuroprotection Against NMDA Toxicity by Tobacco Cembranoids

Although 4R did not block NMDA receptor-mediated PS, preincubation with either 4R or 4S protected against NMDA (Bar Graph B of FIG. 5). Both stereoisomers were active at 20 μM (P<0.001) but, at the concentration tested, 4R was significantly more effective than 4S (t, P<0.005). All subsequent experiments were done with 4R. The effect of 4R was similar whether applied for 1 hr before or for 1 hr after NMDA application (Bar Graph C of FIG. 5). Preincubation with 2 μM 4R in $Ca^{2+}$-free ACSF nullified the protective effect (Bar Graph D of FIG. 5). The depletion of extracellular $Ca^{2+}$ was done by perfusing $Ca^{2+}$-free ACSF until stimulation of incoming fibers failed to elicit PSs. After this, 4R was applied in $Ca^{2+}$-free ACSF for 1 hr. Afterwards, normal $Ca^{2+}$ ACSF was applied for 15-20 min until the field potential returned to approximately its initial value. Only then the slices were challenged with NMDA. The same $Ca^{2+}$ depletion and the additional ACSF washes were done to all the experimental groups in these experiments.

The selective α4β2 antagonist DHβE, (1 μM; Raggenbass, M., and Bertrand, D., J Neurobiol 55:580-589 (2002)), blocked neuroprotection by 2 μM 4R, suggesting that α4β2 was involved (Bar Graph E of FIG. 5).

The dependence on extracellular $Ca^{2+}$ for 4R-induced neuroprotection suggested involvement of $Ca^{2+}$-mediated cell signaling processes. To investigate which cell signaling pathways mediate the neuroprotective effect of 4R, selective inhibitors were used. Each inhibitor was used at a concentration near 10 times the $IC_{50}$ of the enzyme targeted to assure near-complete inhibition.

The role of MEK-1,2 phosphorylation of ERK-1,2 in 4R neuroprotection was tested with 50 μM PD98059. The neuroprotective effect of 4R was not affected significantly but the neuroprotection by nicotine was annulled by PD98059 (Bar Graphs F and G, FIG. 5). The PKC inhibitor 100 nM Ro-31-8220 did not decrease the neuroprotection by 4R, but it did inhibit the effect of nicotine (Bar Graphs H and I, FIG. 5). These results highlight the difference between the mechanism of 4R and nicotine neuroprotection.

Example 7

Roles of L-Type $Ca^{2+}$ Channels and CaM Kinase in 4R Neuroprotection

The roles of L-type $Ca^{2+}$ channels and $Ca^{2+}$ calmodulin-dependent (CaM) kinase were tested by applying 4R in the presence of either 10 μM nifedipine or 9 μM KN-62, respectively. Nifedipine did significantly decrease the effect of 4R but did not inhibit the effect of nicotine (Bar Graph A, FIG. 7). KN-62 partially inhibited (†$P<0.05$) the effect of 4R (Bar Graph B, FIG. 7). The inhibitor of protein kinase A (PKA), 0.5 μM KT5720 partially decreased (†$P<0.05$) the neuroprotective effects of 4R and nicotine (Bar Graphs C and D, FIG. 7). The role of PI3K was tested with 10 nM wortmannin and 10 μM Ly294002. Both PI3K inhibitors significantly decreased the effect of 4R on neuroprotection (Bar Graphs E and F, FIG. 7).

The inhibitor of GSK3, 100 μM SB216763, was significantly more protective when applied after but not before NMDA, suggesting that NMDA challenge activates this proapoptotic enzyme (Bar Graph G, FIG. 7).

Example 8

4R-Mediated Phosphorylation

The 4R-mediated activation by phosphorylation of ERK-1,2 and Akt showed a differential effect. After 1 hr of recovery from dissection, the slices were treated with 4R for 5, 10, 20, 30, 45, or 60 min (FIG. 9). ERK-1,2 was not significantly affected by 4R, but Akt phosphorylation showed a significant increase between 10 and 20 min and returned to control values after 30 min. The 4R-mediated Akt phosphorylation was inhibited by 1 μM DHβE. DHβE did not affect Akt phosphorylation, showing that 4R-mediated Akt phosphorylation was dependent on the activity of the α4β2 nAChR (FIG. 10).

The effect of 4R concentration on the phosphorylation of ERK-1,2, Akt, and GSK3b and GSK3a was tested. Slices were incubated for 20 min with 0.02, 0.05, 0.2, 2, 10, 20, or 40 μM 4R (FIG. 11). ERK-1,2 did not significantly respond to any of the tested 4R concentrations, but Akt and GSK3 showed increased phosphorylation.

Example 9

The Effects of DNQX on the Neuroprotective Effects of Nicotine

Neuroprotection of nicotine was evaluated in the presence of 50 μM DNQX, a selective inhibitor of the AMPA/kainate-type glutamate receptors. Brain slices were perfused with ACSF for 1 hour before the initial population spikes (PSs) were recorded. The NMDA controls were perfused with ACSF for another hour followed by 0.5 mM NMDA for 10 min (FIG. 15.—left bar). A second group was perfused with 1 μM nicotine during 1 hr followed by 0.5 mM NMDA (FIG. 15.—middle bar). This group showed a strong neuroprotective effect expressed as more than 80% recovery. A third group was perfused with 1 μM nicotine during 1 hr in the presence of 50 μM 6,7-dinitroquinoxaline-2,3-dione (DNQX) a selective inhibitor of the AMPA/kainate or non-NMDA glutamate receptors followed by 0.5 mM NMDA (FIG. 15—right bar). The group pretreated with nicotine recovered significantly more activity that the group exposed to nicotine in the presence of DNQX or the group treated only with NMDA ($p<0.05$, N=21).

Example 10

The Effects of DNQX on the Neuroprotective Effects of 4R

Neuroprotection of 4R was evaluated in the presence of 50 μM DNQX, a selective inhibitor of the AMPA/kainate-type glutamate receptors. The experimental conditions were similar to those shown of Example 9. All slices were perfused with ACSF for 1 hr before the initial population spikes (PSs) were recorded; the NMDA controls were then perfused with 50 μM DNQX during 1 hr followed by 0.5 mM NMDA for 10 min (FIG. 16.—left bar demonstrates NMDA unprotected controls); the second group was perfused with 2 μM 4R in the presence of 50 μM DNQX during 1 hr followed by 0.5 mM NMDA (FIG. 16. middle bar demonstrates effect of 4R inhibited by DNQX); the third group was perfused with 2 μM 4R during 1 hr followed by 0.5 mM NMDA (FIG. 16. last bar demonstrates protection by 4R).

Example 11

Memantine Neuroprotects by a Nicotinic Mechanism

The mechanism by which memantine neuroprotects was tested using the rat hippocampal slice model. Neuroprotection was measured using acute rat hippocampal slices and electrophysiological recordings as in Examples 1-4. Experimental conditions were similar to those of Examples 9 and 10.

DHβE was applied for 1 hour followed by 0.5 mM NMDA (FIG. 17. left bar demonstrates the control group). Memantine was perfused for 1 hour followed by 10 minutes of 0.5 mM NMDA (FIG. 17 middle bar.)

Memantine neuroprotective action was inhibited by 1 μM DHβE, a selective inhibitor of the α4β2 receptor (FIG. 17 last bar). Further experiments demonstrated that memantine action was blocked by 10 μM nifedipine, vesamicol and inhibitors of PI3-kinase but not by PD98059 (FIG. 18, FIG. 19, and Table 1). Table 1 demonstrates the pharmacological profile of the two mechanisms (A and B) of nicotinic neuroprotection. Both mechanisms are dependent on the presence of $Ca^{2+}$ and are nicotinic because they are inhibited by dihydro-beta-erythroidine. Mechanism A is initiated by nicotine which stimulates the α4β2 nAChR and increases glutamate release, probably in a subset of synapses. The release of glutamate causes the activation of non-NMDA glutamate receptors. This mechanism A depends on the simultaneous activity of the ERK-1,2 and on the PI3-kinase/Akt cascades as shown by the inhibition of the respective inhibitors. Mechanism B is more complex, it is triggered by inhibition of the α7 nAChRs and triggers a chain of events (see FIG. 12) that lead to synaptic stimulation of NMDA and non-NMDA glutamate receptors that cause Akt dependent but ERK-1,2 independent neuroprotection. Mechanism B is caused by synaptic interaction as proved among others by its inhibition by vesamicol. Vesamicol is an inhibitor of acetylcholine (ACh) release from synaptic vesicles. (Inhibition of neuroprotection: .dwnarw.; No effect on neuroprotection: 0; Not determined: n.d.). All the results were replicated and were significant at least to p<0.05 using ANOVA followed by a post hoc test.

The dose-response curve for memantine neuroprotection was bell-shaped (FIG. 20B). Memantine neuroprotects in a dose-dependent manner at concentrations below 3 μM but this effect decreases at higher concentrations. The neuroprotective portion of this curve starts near the $IC_{50}$ of memantine for the inhibition of the α7 nAChRs ($IC_{50}$=0.34 μM), while the decrease of the neuroprotection starts near the $IC_{50}$ for the NMDA receptor ($IC_{50=5.1}$ μM). The homologous curve for 4R is sigmoid revealing that it does not have any untoward effect in the range of concentrations used (FIG. 20A).

Memantine protects the rat hippocampal slice from the NMDA-induced toxicity. The mechanism of neuroprotection is similar (if not identical) to the one underlying the action of 4R but different from that of nicotine. In this system, 4R is a more efficient neuroprotective drug than memantine, due to the fact that memantine dose-response curve is bell-shaped while 4R is sigmoid. These results support the notion that 4R could be an efficacious therapy for treatment of moderate to severe Alzheimer Disease.

TABLE 1

| | | Effect on the neuroprotection caused by: | | | |
|---|---|---|---|---|---|
| Main | | Mechanism A | Mechanism B | | |
| Target | Inhibitor | Nicotine | 4R | MLA | Memantine |
| α4β2 | L μM DHIβE | ↓ | ↓ | ↓ | ↓ |
| NMDA receptors | 4 μMAPV | 0 | ↓ | ↓ | ↓ |
| AMPA-receptors | 50 μM DNQX | ↓ | ↓ | n.d. | n.d. |
| L-type VGCC | 10 μM Nifedipine | 0 | ↓ | ↓ | ↓ |
| CaM kinases | 9 μMKN-62 | 0 | ↓ | ↓ | n.d. |
| ERK-1,2 kinase | 10 μM PD98059 | ↓ | 0 | 0 | 0 |
| PKC | 0.1 μM Ro31-8220 | ↓ | 0 | n.d. | 0 |
| PI3-Kinase | 10 μM Ly294002 | ↓ | 0 | n.d. | ↓ |
| PI3-Kinase | 10 μM Wortmannin | ↓ | ↓ | n.d. | ↓ |
| Synaptic ACh release | 50 μM Vesarnicol | 0 | ↓ | n.d. | ↓ |

Example 12

4R Decreases the Infarct Size in an In Vivo Model of Cerebral Stroke

The effects of 4R on infarct size was tested using a model of human cerebral stroke known as the middle cerebral artery occlusion (MCAO).

Adult male Sprague-Dawley rats weighing 250-300 g were subjected to left middle cerebral artery occlusion (MCAO) as previously described (Xu Z. et al., Biochem Biophys Res Commun 322:440-446 (2004). Surgical procedures were performed by sterile/aseptic techniques in accordance with institutional guidelines. Rats were anesthetized with a ketamine/xylazine solution (10 mg/kg, IP). MCAO was induced by the intraluminal suture method as previously described (Belayev L. et al., Brain Res 833:181-190 (1999)). Briefly, the left common carotid artery (CCA) was exposed through a midline incision and carefully dissected free from surrounding nerves and fascia. The occipital artery branches of the external carotid artery (ECA) were isolated and the occipital artery and superior thyroid artery branches of the ECA were coagulated. The ECA was dissected further distally. The internal carotid artery (ICA) was isolated and carefully separated from the adjacent vagus nerve, and the pterygopalatine artery was ligated close to its origin with a 5-0 silk suture. Then, a 4 cm length 3-0 surgical monofilament nylon suture (Harvard Apparatus, Holliston, Mass.) was coated with poly-L-lysine with its tip rounded by heating near a flame. The filament was inserted from the ECA into the ICA and then into the Circle of Willis to occlude the origin of the left middle cerebral artery (MCA). The suture was inserted 18 to 20 mm from the bifurcation of the CCA to occlude the MCA. After 24 hours the animals were sacrificed and the infarct volume determined as described below.

Measurement of Infarct Volume and Neurological Function

Immediately after sacrifice the brains were removed, sliced into 2 mm coronal sections (approximately +3.0 to −5.0 from bregma) using a brain matrix, incubated in a 2%2,3,5-triphenyltetrazolium chloride (TTC) solution for 30 minutes at 37.degree. C., and then transferred into a 10% formaldehyde solution for fixation. TTC, a colorless salt, is reduced to form an insoluble red formazan product in the presence of a functioning mitochondrial electron transport chain. Thus, the infracted region lacks staining and appears white, whereas the normal non-infracted tissue appears red. Infarct area of slices was calculated by capturing the images with a digital camera and using Image Pro software. All infarct area measurements were calculated with a 2 mm distance between the slices. Using these measurements, the total infarct volume was calculated for each brain. The volume of infarction was calculated by an investigator who was blinded to the experimental groups. Infarct volumes were analyzed by ANOVA; P<0.05 was regarded as significant.

Determination of 4R Effect

MCAO was performed on fifteen adult male Sprague-Dawley rats, assigned to the treatment group (N=9) and the control group (N=6). The rats in the treatment group received 6.12 μg of 4R in 10% DMSO/saline, administered intraarterially immediately prior to pMCAO. Vehicle was 10% DMSO/saline. The animals were sacrificed 24 hours after pMCAO. Brains were extracted, cut in slices using a brain matrix and incubated with 2,3,5-triphenyltetrazolium chloride (TTC) to quantify the infarct volume.

FIG. 21 illustrates that the size of the necrotic area is much smaller in brains of rats treated with 4R than in vehicle-treated controls. The statistical analysis of all data demonstrate that 4R attenuated the infarct volume by 68% in the cerebral cortex (p<0.05) and by 34% in the striatum (p<0.05) (FIG. 22).

Treatment with microgram amounts of 4R significantly ameliorated the extent of infracted tissue in brains of rats subjected to middle cerebral artery occlusion. These results extend our findings with the acute hippocampal slice to a living brain and indicate that 4R is a candidate drug for treatment of stroke.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for inhibiting neuronal damage comprising administering to a person in need thereof an effective amount of a compound of the formula:

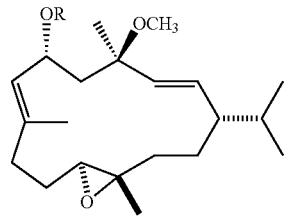

wherein R is H or COCH$_3$.

2. The method of claim 1 wherein said compound is administered in an amount sufficient to achieve a concentration between about 200 nM to about 40 μM.

3. The method of claim 1 wherein the person has suffered, suffers from, or is at risk for a neurodegenerative disease.

4. The method of claim 3 wherein said neurodegenerative disease is a delayed effect of stroke.

5. The method of claim 1 wherein said compound is administered during prenatal or postnatal treatment.

* * * * *